(12) United States Patent
Pastan et al.

(10) Patent No.: US 7,572,887 B2
(45) Date of Patent: Aug. 11, 2009

(54) GENE EXPRESSED IN PROSTATE CANCER, METHODS AND USE THEREOF

(75) Inventors: Ira Pastan, Potomac, MD (US); Tapan K. Bera, Germantown, MD (US); Byungkook Lee, Potomac, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/552,515

(22) PCT Filed: Apr. 5, 2004

(86) PCT No.: PCT/US2004/010588

§ 371 (c)(1),
(2), (4) Date: Oct. 6, 2005

(87) PCT Pub. No.: WO2004/092213

PCT Pub. Date: Oct. 28, 2004

(65) Prior Publication Data

US 2006/0194204 A1    Aug. 31, 2006

Related U.S. Application Data

(60) Provisional application No. 60/461,399, filed on Apr. 8, 2003.

(51) Int. Cl.
C07K 14/00 (2006.01)
C07H 21/04 (2006.01)
C12N 15/00 (2006.01)
C12Q 1/68 (2006.01)

(52) U.S. Cl. ............... 530/350; 530/300; 536/23.5; 435/6; 435/320.1

(58) Field of Classification Search ........... 530/350; 536/23.1
See application file for complete search history.

(56) References Cited

U.S. PATENT DOCUMENTS 5,851,764 A    12/1998    Fisher et al.

FOREIGN PATENT DOCUMENTS

| WO | WO 99/67384 | 12/1999 |
|----|----|----|
| WO | WO 00/12706 | 3/2000 |
| WO | WO 01/75067 | 10/2001 |
| WO | WO 01175067 A2 * | 10/2001 |
| WO | WO 02/18584 | 3/2002 |
| WO | WO 02/24718 | 3/2002 |
| WO | WO 03/042370 * | 5/2003 |

OTHER PUBLICATIONS

Bera et al (PNAS, 2004, 101:3059-3064, IDS).*
Bera et al (PNAS, 2004, 101:3059-3064).*
Tockman et al (Cancer Res., 1992, 52:2711s-2718s).*
Bera et al (PNAS, 2004, 101:3059-3064).*
Das et al (poster presentation from the AACR meeting, 2007, Exhibit D).*
Tockman et al (Cancer Res., 1992, 52:2711s-2718s).*
Lee et al (J. Immunol., 1999, 163:6292-6300).*
Kirkin et al (1998, APMIS, 106 : 665-679).*
Chaux et al, (Int J Cancer, 1998, 77: 538-542).*
Boon (Adv Can Res, 1992, 58:177-210).*
Celis (J of Clinical Investigation, 2002, 110:1765-1768).*
Rolland (Advanced Drug Delivery Reviews, 2005, 57:669-673).*
McCormick (Nature Reviews, 2001, 1:130-141).*
Strausberg et al., EMBL Accession No. BC047903, Mar. 5, 2003.
Drmanac et al., EMBL Accession No. AAS79675, Feb. 13, 2002.
Drmanac et al., EMBL Accession No. ABG15488, Feb. 18, 2002.
Sun et al., EMBL Accession No. AAD38831, Sep. 23, 2002.
Sun et al., EMBL Accession No. AAE24066, Sep. 23, 2002.
Bera et al., "NGEP, a gene encoding a membrane protein detected only in prostate cancer and normal prostate", *PNAS*, vol. 101, No. 9, pp. 3059-3064, Mar. 2, 2004.
Ota et al., GENBANK Accession No. AK057322, Oct. 31, 2001.
Strausberg et al., GENBANK Accession No. BC028162, Oct. 28, 2002.
Strausbert et al., GENBANK Accession No. BC038852, Oct. 28, 2002.
Strausberg et al., GENBANK Accession No. BC047903, Mar. 4, 2003.
GENBANK Accession No. XM_297689, Apr. 10, 2003.
Holmes et al., GENBANK Accession No. AC104841, Dec. 21, 2001.

* cited by examiner

*Primary Examiner*—Laura B Goddard
(74) *Attorney, Agent, or Firm*—Klarquist Sparkman, LLC

(57) ABSTRACT

A polypeptide is disclosed that is specifically detected in the cells of the prostate, termed Splice Variant-Novel Gene Expressed in Prostate (SV-NGEP). Polynucleotides encoding SV-NGEP are also disclosed, as are vectors including these polynucleotides. Host cells transformed with these polynucleotides are also disclosed. Antibodies and immunoconjugages are disclosed that specifically bind SV-NGEP. Methods are disclosed for using an NGEP polypeptide, an antibody that specifically binds SV-NGEP, or a polynucleotide encoding SV-NGEP. Assays are disclosed for the detection of prostate cancer. Pharmaceutical compositions including an SV-NGEP polypeptide, an antibody that specifically binds SV-NEGP, or a polynucleotide encoding SV-NGEP are also disclosed. These pharmaceutical compositions are of use in the treatment of prostate cancer.

21 Claims, 6 Drawing Sheets

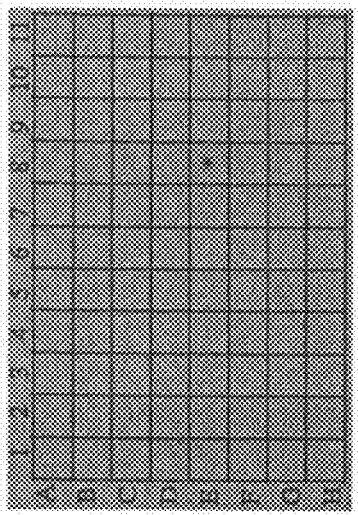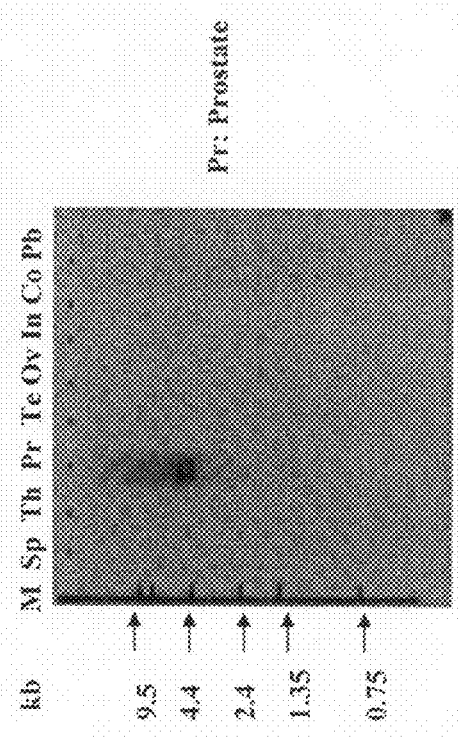
FIG. 2A
FIG. 2B

```
aaaagatagatcctgctccaggagccgggaagcctcgccggccagctgtcgctggcacctccctgctgcttcctgg
cccattgcaggcaaggtgagggcATGCGAATGGCTGCCACTGCCTGGGCGGGGCTCCAAGGGCCACCCTCCCCACCCT
CTGTCCCGCAGTGAGGACGGGACTCTACTGCCCGAGACCAGGCTCACGCTGAGAGGTGGGCATGCCTGAGACCTCTT
CCGGAAGCCACTGTGCCAGGAGCAGGATGCTGCGGCGACCAGGGCGACGGGCCCAGGAGAGAGACAGCACCGTCCGATCGATGTGAGC
CCCCTGAGGCAGAGAAGAGGGGCTCTTACGGAGCACAGCCCCGGAGACTTCGTCCTCGTTGGGAGGAGGAGCCAAGCGGCCGCTG
CAGAGCTGGGAGTCCTGCAAGCCCCGGACCAGACAGCACCAGGAGACCTGGCGGGAGACCTTTTCTTGGATAATCTTCGTGCGGCTGG
AGGACAGTGCCGCCCGGGACAGAGGACGTCCAGGACGGGCTGAAGCTGCCCTGGAAGCTGCTACTACGCCCTCTCAGCGCCTCCTGGGCTGTGT
CTGTGTGTAGACCAGCAGGACGTCCAGGACGGGCTGAAGCTGCCCTGGAAGCTGCCCTTGCTACTACGCCCTCTCAGCGCCTCCTGGGCTGTGCT
CTGCTACTACGCCCGAAGACCTGCGCATCCCCAACGTCCTGCTGGAGTGACAACCAGGACACCTTCTTCACAAGCACCAAGAGGACCAAAATTCT
TGCTGGCATGGCTGGGCATCCCCAACGTCCTGCTGGAGTGACAACCAGGACACCTTCTTCACAAGCACCAAGAGGACCAAAATTCT
AGAGTGAACAAGCTGCCACGCTTCCTCGGAGTGACAACCAGGACACCTTCTTCACAAGCACCAAGAGGACCAAAATTCT
GTTTGAGATCCTGCCAAGACCCGTATGGCCACGAACCCCTCAAGACGCCCAGAGGGCCCGCAGGCTCCACGCTCAACCAG
TCCTCAGTGCCGCCTTCCCCCTGACACTGGGGCCTGTGGGACAAGTACCAGCCCTGGACCACGTGCGCAGGTACTT
CGCCAAGTCCTTTCCAGCACTGGGCCCTCTACTTCGCCTGCTCTGTGTTCTCAGACATACCCACGCAGGAACTGTGTGGCAGCAGTGGGCACAC
CGGGGAGAAGGTGGCCCTCTACTTCGCCTGCTCTGTGTTCTCAGACATACCCACGCAGGAACTGTGTGGCAGCAGTGGGCACAC
TGGTGTTCCTGGTGGGCTGCTCTGACTGCCCTTTGTCCTGACTTGTTCATGGCACTGTGGGCCGTGCTGCTGAGTGGAAGCGGAAGACG
ATGCCCACCTTTGCCTGACTGCCCCTTTGTCCTGACTTGTTCATGGCACTGTGGGCCGTGCTGCTGAGTGGAAGCGGAAGAGCG
CCACGCGGCACCGTGTTCTTCAGCTTGTTCTGACTTGTTCATGGCACTGTGGGCCGTGCTGCTGAGTGGAAGCGGAAGAGCG
CCACGCTGCTCCGCTACCGCTGGGACTTGTCTGACTACGAGGACACTGAGGAGAGCCCTCGGCCTCCAGTTTGCCGCCTCAGCC
CCATGACAGCCCCGAACCCCATCACGGGTGAAGGACGAGCCCTACTTCCCTGCCTGGTGTCATTGCCTGTCATTGCCTCACGGGGTTCCTGGC
CGGCTCTGTGGTGATCGTGGTGATGGCAACACCCTTCTGCCAGCCTGGGCCTTCGCCATCGCCACAGTCGTGCCCACGGGTCGTAGTG
CCATCGTGTGTCCAGGTCGGGCAACACCCTCTCCAAGATCTATGTATTCCTGGCCCACGTCCTGACACGTTCGTCAACTTCTCAGTTCTTCATCTTCAGTTGTCAACTTCTCACCCGTCTACA
AACCTCGTCTTCATCCTCATCCTCCAAGATCTATGTATTCCTGGCCCACGTCCTGACACGTTCGTCAACTTCTCAGTTGTTCATCTTCAGTTGTCAACTTCTCACCCGTCTACA
CCAGACCAAGTTCGAGGACGCCTTCGTGTGGGATACCCAGGAGCTCCTGGTCATCATGGTGGGCAAGCAGGTCATCAACAACATGCAGGA
TTGCCTTCTTCAAGGGCAGGTTTGTGGGATACCCAGGAGCTCCTGGTCATCATGGTGGGCAAGCAGGTCATCAACAACATGCAGGA
GCTGGAGCTGCTGATCGACTGGCACAGGACTGGTGGCAGAAGTTCGGTCGCTTCCCCTGTGAGGGTTGTTGACGAGTACCTGAAATGGTG
GGCTAGCAGGGGCCCTGGGAGACCACTATGAGCTTGTTGCCCTGTGAGGGTTGTTGACGAGTACCTGAAATGGTG
CTGCAGTTCGGCTTGGACGCGCAAGTTCGTTCGTCGGCAAGTTCGTCGCGCGGCAGTTGGGACCAATCGGCGCATCTGGT
GATCCGGCTTGGACGCGCAAGTTCGTCGCGCACCATCTTCGTGGCCGCCGTCGGCAAGTTCGTCGCGCGGCAGTTGGGACCAATCGGCGCATCTGGT
TCCACATCCTGGCGGGCTCACGCAGTGGACCCGGCCCACGACCTGCCGCCGGCTTTCCGGGATGACATTATTCCCCAGACCTACTGGAATC
CGCGCCTACTACGGGTGAGACCGCACAACCGCACGTGCAGGTATCGGGCTTTCCGGGATGACATTATTCCCCAGACCTACTGGAATC
TTCTTGCCATCCGCCTTGGCCTTCGTGCCCATTCGTGTTTGAGCATGTGGTTTTCTCGTTGGCCGCCTCCTGGACCTCCTGGTG
CCTGACATCCCAGAGTTCTGTGGAGATCAAAGTGAAGCGGGAGTACTACCTGGCTAAGGCACTGGCTGAGAATGAGGT
TCTTTTGGAACGAACGGAACAAGGATGCACAGCCCAAGGGCTCAGCTCCCACTGGACACCCTTCACGGTTC
CAAGGCCAGCCAGCTGCAGCAGTGAcgccctggaaggacaactgtggtccttaggggagtggccctcctgagccctgc
gagcaggcgctgctttcctcttcctccaggcagccgctgtgaaccgctgcgtgttgcctcatctctggcacat
tgcctgttccccccagcgccggcttctctcagacgcctgcactccatccccggcagggaggaccgtcagctca
caaggccctcttgttttcctgccccagacataagccaaggggccctgcacccaagggaccctgcctgggcct
cccaggcccctggacacagttcctccaggcaggtgggctttgggtcctgcgccgccccctggccacatgccctct
cctcttacactggtgaccttcgaatgt    Fig. 3
```

MRMAATAWAGLQGPPLPTLCPAVRTGLYCRDQAHAERWAMTSETSSGSHCARSRMLRRRAQEEDSTVLIDVSPPEAEKRG
SYGSTAHASEPGGQQAAACRAGSPAKPRIADFVLVWEEDLKLDRQQDSAARDRTDMHRTWRETFLDNLRAAGLCVDQQDV
QDGNTTVHYALLSASWAVLCYYAEDLRLKLPLQELPNQASNWSAGLLAWLGIPNVLLEVVPDVPPEYYSCRFRVNKLPRF
LGSDNQDTFFTSTKRHQILFEILAKTPYGHEKKNLLGIHQLLAEGVLSAAFPLHDGPFKTPPEGPQAPRLNQRQVLFQHW
ARWGKWNKYQPLDHVRRYFGEKVALYFAWLGFYTGWLLPAAVVGTLVFLVGCFLVFSDIPTQELCGSKDSFEMCPLCLDC
PFWLLSSACALAQAGRLFDHGGTVFFSLFMALWAVLLLEYWKRKSATLAYRWDCSDYEDTEERPRPQFAASAPMTAPNPI
TGEDEPYFPERSRARIRMLAGSVVIVVMVAVVVMCLVSIILYRAIMAIVVSRSGNTLLAAWASRIASLTGSVVNLVFILL
SKIYVSLAHVLTRWEMIHRTQTKFEDAFTLKVFIFQFVNFYSSPVYIAFFKGRFVGYPGNYHTLFGVRNEECAAGGCLIEL
AQELLVIMVGKQVINNMQEVLIPKLKGWWQKFRLRSKKRKAGASAGASQGPWEDDYELVPCEGLFDEYLEMVLQFGFVTI
FVAACPLAPLFALLNNWVEIRLDARKFVCEYRRPVAERAQDIGIWFHILAGLTHLAVISNAFLLAFSSDFLPRAYYRWTR
AHDLRGFLNFTLARAPSSFAAAHNRTCRYRAFRDDDGHYSQTYWNLLAIRLAFVIVFEHVVFSVGRLLDLLVPDIPESVE
IKVKREYYLAKQALAENEVLFGTNGTKDEQPKGSELSSHWTPFTVPKASQLQQ

Fig. 4

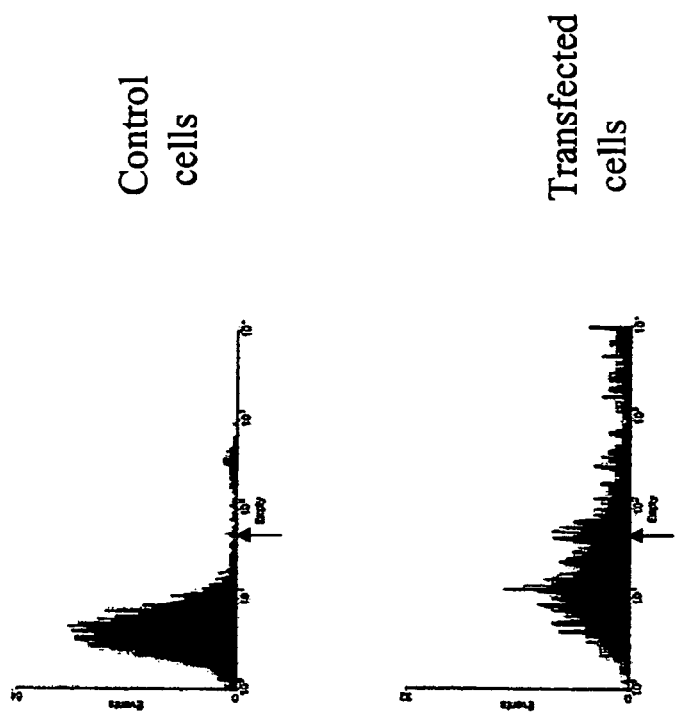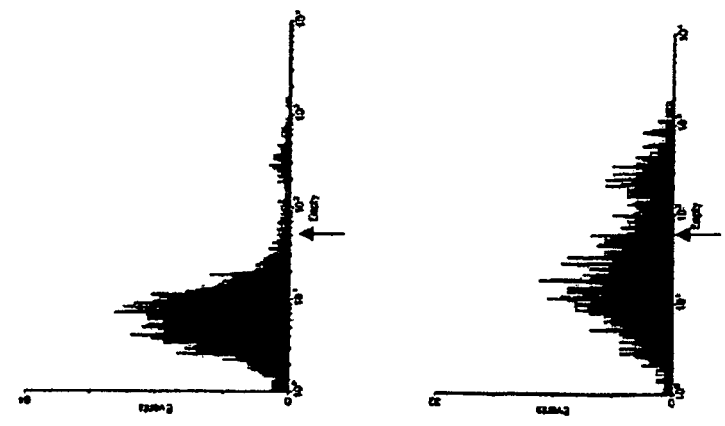
Figs. 6A-B

GENE EXPRESSED IN PROSTATE CANCER, METHODS AND USE THEREOF

CROSS REFERENCE TO RELATED APPLICATIONS

This is the U.S. National Stage of International Application No. PCT/US2004/010588, filed Apr. 5, 2004, which was published in English under PCT Article 21(2), and which claims the benefit of U.S. Provisional Application No. 60/461,399, filed Apr. 8, 2003, which is incorporated by reference herein in its entirety.

PRIORITY CLAIM

1. Field of the Invention

This disclosure relates the prostate, specifically to polypeptides expressed specifically in the prostate. The disclosure further relates to detection and treatment of prostate cancer.

2. Background of the Invention

Cancer of the prostate is the most commonly diagnosed cancer in men and is the second most common cause of cancer death (Carter and Coffey, *Prostate* 16:39-48, 1990; Armbruster et al., *Clinical Chemistry* 39:181, 1993). If detected at an early stage, prostate cancer is potentially curable. However, a majority of cases are diagnosed at later stages when metastasis of the primary tumor has already occurred (Wang et al., *Meth. Cancer Res.* 19:179, 1982). Even early diagnosis is problematic because not all individuals who test positive in these screens develop cancer.

Prostate specific antigen (PSA) is a 240 amino acid member of the glandular kallikrein gene family (Wang et al., 1982, supra; Wang et al., *Invest. Urology*, 17:159, 1979; Bilhartz et al., *Urology*, 38:95, 1991). PSA is a serine protease, produced by normal prostatic tissue, and secreted exclusively by the epithelial cells lining prostatic acini and ducts (Wang et al., 1982, supra; Wang et al., 1979, supra; Lilja et al., *World J. Urol.*, 11:188-191, 1993). Prostate specific antigen can be detected at low levels in the sera of healthy males without clinical evidence of prostate cancer. However, during neoplastic states, circulating levels of this antigen increase dramatically, correlating with the clinical stage of the disease (Schellhammer et al., *Urologic Clinics of North America* 20:597, 1993; Huang et al., *Prostate* 23:201, 1993). Prostate specific antigen is now the most widely used marker for prostate cancer. However, there clearly is a need to identify additional antigens to aid in the diagnosis of prostate cancer, and for use as therapeutic agents.

Present treatment for prostate cancer includes radical prostatectomy, radiation therapy, or hormonal therapy. With surgical intervention, complete eradication of the tumor is not always achieved and the observed re-occurrence of the cancer (12-68%) is dependent upon the initial clinical tumor stage (Zietman et al., *Cancer* 71:959, 1993). Thus, alternative methods of treatment including prophylaxis or prevention are desirable.

Immunotherapy is a potent new weapon against cancer. Immunotherapy involves evoking an immune response against cancer cells based on their production of target antigens. Immunotherapy based on cell-mediated immune responses involves generating a cell-mediated response to cells that produce particular antigenic determinants, while immunotherapy based on humoral immune responses involves generating specific antibodies to cells that produce particular antigenic determinants.

Cancer cells produce various proteins that can become the target of immunotherapy; antigenic determinants normally present on a specific cell type can also be immunogenic. For example, it has been shown that tumor infiltrating lymphocytes target and recognize antigenic determinants of the protein MART-1, produced by both normal melanocytes and malignant melanoma cells. Furthermore, active or passive immunotherapy directed against MART-1 or peptides of it that bind to MHC Class I molecules (epitopes of HLA A2, in particular) results in the destruction of melanoma cells as well as normal cells that produce MART-1 (Kawakami et al., *J. Immunol.* 21:237, 1998). The tissue specificity of PSA has made it a potential target antigen for active specific immunotherapy (Armbruster et al., *Clin. Chemistry* 39:181, 1993; Brawer et al., *Cancer Journal Clinic* 39:361, 1989), especially in patients who have undergone a radical prostatectomy in which the only PSA expressing tissue in the body should be in metastatic deposits.

Recent studies using in vitro immunization have shown the generation of CD4 and CD8 cells specific for PSA (Peace et al., *Cancer Vaccines: Structural Basis for Vaccine Development* (Abstract), 1994; Correale et al., *9th International Congress of Immunology* (Abstract), 1995), and methods for inducing an immune response against PSA include the use of viral vectors incorporating DNA encoding PSA (e.g. see U.S. Pat. No. 6,165,460; Hodge et al., *Cancer* 63:231, 1995). Discovery of additional antigens expressed by the prostate gland can similarly be used to design immunotherapy methods for prostate cancer.

SUMMARY OF THE INVENTION

A new polypeptide is disclosed herein that is specifically detected in the cells of the prostate. This polypeptide is termed Splice Variant-Novel Gene Expressed in Prostate (SV-NGEP). Polynucleotides encoding SV-NGEP are also disclosed herein, as are vectors including polynucleotides encoding SV-NGEP, and host cells transformed with these polynucleotides. Antibodies that specifically bind SV-NGEP are also disclosed.

Methods for using an SV-NGEP polypeptide, an antibody that specifically binds SV-NGEP, or a polynucleotide encoding SV-NGEP are also disclosed. A specific, non-limiting example of a method of use is an assay to detect prostate cancer. Also disclosed are pharmaceutical compositions including a SV-NGEP polypeptide, an antibody that specifically binds SV-NGEP, or a polynucleotide encoding SV-NGEP. In one embodiment, the pharmaceutical composition is used to treat prostate cancer.

The foregoing and other features and advantages will become more apparent from the following detailed description of several embodiments, which proceeds with reference to the accompanying figures.

BRIEF DESCRIPTION OF THE FIGURES

FIGS. 2A-2B are a set of digital images showing tissue specific expression of mRNA encoding SV-NGEP. FIG. 2A is a digital image of a RNA hybridization of a multiple tissue dot-blot containing mRNA from 61 normal human cell types or tissues using NGEP cDNA as probe. SV-NGEP expression is observed only in prostate (E8) and no detectable expression was seen in brain (A1), heart (A4), lung (A8), kidney (A7), and pancreas (B9). FIG. 2B is a Northern blot analysis of SV-NGEP in different normal tissues. The matured transcript is about 4.4 and 4.6 kb in size and is expressed only in prostate.

FIG. 3 is the nucleic acid sequence of SV-NGEP (SEQ ID NO: 2).

FIG. 4 is the amino acid sequence of SV-NGEP (SEQ ID NO: 1).

FIGS. 6A-B are a set of data plots showing staining with a mouse (FIG. 6A) and a rabbit (FIG. 6B) antibody to SV-NGEP. FACS analysis of cells transfected with SV-NGEP. Single parameter histograms for the gated transfected cells for vector alone control (top) and SV-NGEP (bottom) are shown. Cells were transfected with anti-SV-NGEP sera from either mouse or rabbit followed by phycoerythrin-labeled secondary antibodies. The arrow represents the boundary of negative and positively stained cell peak.

SEQUENCE LISTING

Figure 1:
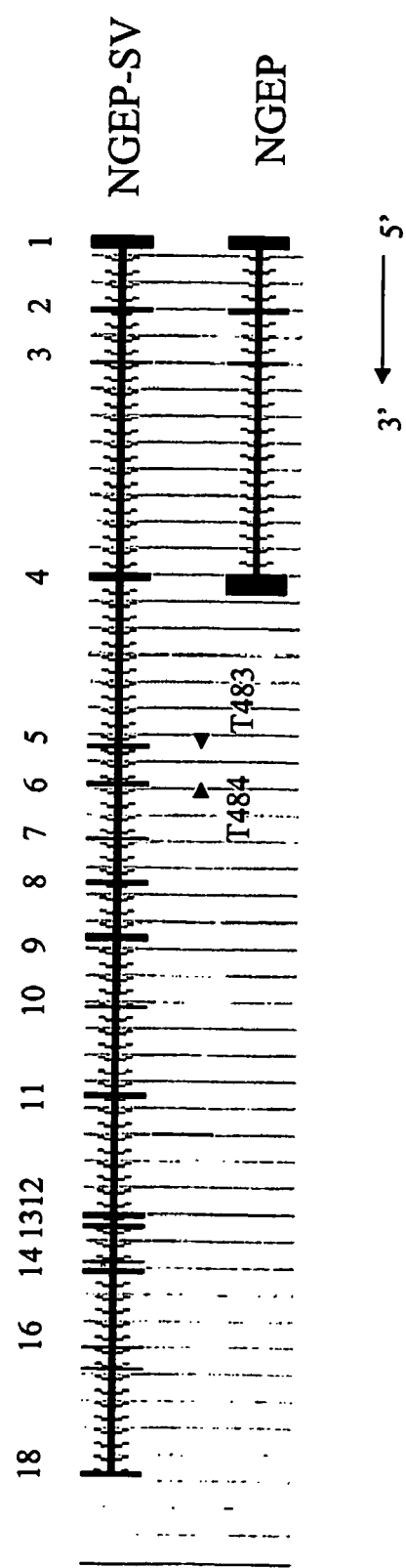
FIG. 1 is a schematic diagram of NGEP and SV-NGEP genes. The primers T483 and T 484 were used to generate a PCR fragment which was used as a radio-labeled probe for Dot blot and Northern analysis.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 is a polypeptide sequence of a SV-NGEP polypeptide.

SEQ ID NO: 2 is a polynucleotide sequence of a polynucleotide encoding SV-NGEP.

SEQ ID NOs: 3-10 are fragments of SV-NGEP that are predicted to specifically bind MHC Class I.

SEQ ID NO: 11 is the nucleic acid sequence of the T483 primer.

SEQ ID NO: 12 is the nucleic acid sequence of the T484 primer.

DETAILED DESCRIPTION

A novel gene product expressed in cells of the normal prostate and prostate cancer, termed SV-Novel Gene Expressed in Prostate (SV-NGEP), is disclosed herein.

After defining some of the terms used herein, the discussion below sets forth the discovery of the nature of the SV-NGEP protein, nucleic acid sequences encoding SV-NGEP, and the expression of this protein. As SV-NGEP is expressed in prostate cancer, it is of use in detecting prostate cancer cells. Diagnostic kits for SV-NGEP are thus disclosed.

Antibodies that specifically bind SV-NGEP are also disclosed herein. These antibodies are of use in detection assays, as well as in the production of immunoconjugates, such as immunotoxins, which can be used to target prostate cancer.

Nucleic acids encoding SV-NGEP, or an SV-NGEP polypeptide, can be used to produce an immune response against prostate cancer cells. Thus, pharmaceutical compositions including SV-NGEP, or a nucleic acid encoding SV-NGEP are also disclosed.

I. Abbreviations

CTL: cytotoxic T lymphocyte
DT: diphtheria toxin
EM: effector molecule
MHC: Major Histocompatibility Complex
NGEP: Novel Gene Expressed in Prostate PE: *Pseudomonas* exotoxin
SV-NGEP: Splice Variant-Novel Gene Expressed in Prostate II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes. "Epitope" or "antigenic determinant" refers to a site on an antigen to which B and/or T cells respond. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance.

An antigen can be a tissue-specific antigen, or a disease-specific antigen. These terms are not exclusive, as a tissue-specific antigen can also be a disease specific antigen. A tissue-specific antigen is expressed in a limited number of tissues, such as a single tissue. Specific, non-limiting examples of a tissue specific antigen are a prostate specific antigen. A disease-specific antigen is expressed coincidentally with a disease process. Specific non-limiting examples of a disease-specific antigen are an antigen whose expression correlates with, or is predictive of, tumor formation, such as prostate cancer. A disease specific antigen may be an antigen recognized by T cells or B cells.

Amplification: Of a nucleic acid molecule (e.g., a DNA or RNA molecule) refers to use of a technique that increases the number of copies of a nucleic acid molecule in a specimen. An example of amplification is the polymerase chain reaction, in which a biological sample collected from a subject is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification may be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Antibody: Immunoglobulin molecules and immunologically active portions of immunoglobulin molecules, i.e., molecules that contain an antigen binding site that specifically binds (immunoreacts with) an antigen.

A naturally occurring antibody (e.g., IgG, IgM, IgD) includes four polypeptide chains, two heavy (H) chains and two light (L) chains interconnected by disulfide bonds. However, it has been shown that the antigen-binding function of an antibody can be performed by fragments of a naturally occurring antibody. Thus, these antigen-binding fragments are also intended to be designated by the term "antibody." Specific, non-limiting examples of binding fragments encompassed within the term antibody include (i) a Fab fragment consisting of the $V_L$, $V_H$, $C_L$ and $C_{H1}$ domains; (ii) an $F_d$ fragment consisting of the $V_H$ and $C_{H1}$ domains; (iii) an Fv fragment consisting of the VL and VH domains of a single arm of an antibody, (iv) a dAb fragment (Ward et al., Nature 341:544-546, 1989) which consists of a $V_H$ domain; (v) an isolated complimentarily determining region (CDR); and (vi) a $F(ab')_2$ fragment, a bivalent fragment comprising two Fab fragments linked by a disulfide bridge at the hinge region.

Immunoglobulins and certain variants thereof are known and many have been prepared in recombinant cell culture (e.g., see U.S. Pat. No. 4,745,055; U.S. Pat. No. 4,444,487; WO 88/03565; EP 256,654; EP 120,694; EP 125,023; Faoulkner et al., Nature 298:286, 1982; Morrison, J. Immunol. 123:793, 1979; Morrison et al., Ann Rev. Immunol 2:239, 1984).

Animal: Living multi-cellular vertebrate organisms, a category that includes, for example, mammals and birds. The term mammal includes both human and non-human mammals. Similarly, the term "subject" includes both human and veterinary subjects.

Conservative variants: "Conservative" amino acid substitutions are those substitutions that do not substantially affect or decrease an activity or antigenicity of SV-NGEP. Specific, non-limiting examples of a conservative substitution include the following examples:

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The term conservative variation also includes the use of a substituted amino acid in place of an unsubstituted parent amino acid, provided that antibodies raised to the substituted polypeptide also immunoreact with the unsubstituted polypeptide. Non-conservative substitutions are those that reduce an activity or antigenicity.

cDNA (complementary DNA): A piece of DNA lacking internal, non-coding segments (introns) and regulatory sequences that determine transcription. cDNA is synthesized in the laboratory by reverse transcription from messenger RNA extracted from cells.

Degenerate variant: A polynucleotide encoding an SV-NGEP polypeptide that includes a sequence that is degenerate as a result of the genetic code. There are 20 natural amino acids, most of which are specified by more than one codon. Therefore, all degenerate nucleotide sequences are included in this disclosure as long as the amino acid sequence of the SV-NGEP polypeptide encoded by the nucleotide sequence is unchanged.

Diagnostic: Identifying the presence or nature of a pathologic condition, such as, but not limited to, prostate cancer. Diagnostic methods differ in their sensitivity and specificity. The "sensitivity" of a diagnostic assay is the percentage of diseased individuals who test positive (percent of true positives). The "specificity" of a diagnostic assay is 1 minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" is the probability of development (e.g., severity) of a pathologic condition, such as prostate cancer, or metastasis.

Epitope: An antigenic determinant. These are particular chemical groups or peptide sequences on a molecule that are antigenic, i.e. that elicit a specific immune response. An antibody specifically binds a particular antigenic epitope on a polypeptide. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see e.g., Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (e.g., metallothionein promoter) or from mammalian viruses (e.g., the retrovirus long terminal repeat; the adenovirus late promoter; the *vaccinia* virus 7.5K promoter) can be used. Promoters produced by recombinant DNA or synthetic techniques may also be used to provide for transcription of the nucleic acid sequences.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies.

Immunoconjugate: A covalent linkage of an effector molecule to an antibody. The effector molecule can be a toxin. Specific, non-limiting examples of toxins include, but are not limited to, abrin, ricin, *Pseudomonas* exotoxin (PE, such as PE35, PE37, PE38, and PE40), diphtheria toxin (DT), saporin, restrictocin, or modified toxins thereof, or other toxic agents that directly or indirectly inhibit cell growth or kill cells. For example, PE and DT are highly toxic compounds that typically bring about death through liver and heart toxicity in humans. PE and DT, however, can be modified into a form for use as an immunotoxin by removing the native targeting component of the toxin (e.g., domain Ia of PE and the B chain of DT) and replacing it with a different targeting moiety, such as an antibody. A "chimeric molecule" is a targeting moiety, such as a ligand or an antibody, conjugated (coupled) to an effector molecule. The term "conjugated" or "linked" refers to making two polypeptides into one contiguous polypeptide molecule. In one embodiment, an antibody is joined to an effector molecule (EM). In another embodiment, an antibody joined to an effector molecule is further joined to a lipid or other molecule to a protein or peptide to increase its half-life in the body. The linkage can be either by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule.

Immunogenic peptide: A peptide which comprises an allele-specific motif or other sequence such that the peptide will bind an MHC molecule and induce a cytotoxic T lymphocyte ("CTL") response, or a B cell response (e.g. antibody production) against the antigen from which the immunogenic peptide is derived.

In one embodiment, immunogenic peptides are identified using sequence motifs or other methods, such as neural net or polynomial determinations, known in the art. Typically, algorithms are used to determine the "binding threshold" of peptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide. In one embodiment, a conserved residue is one where the MHC structure may provide a contact point with the immunogenic peptide.

Immunogenic composition: A composition comprising an SV-NGEP polypeptide that induces a measurable CTL response against cells expressing SV-NGEP polypeptide, or induces a measurable B cell response (e.g. production of antibodies that specifically bind SV-NGEP) against an SV-NGEP polypeptide. It further refers to isolated nucleic acids encoding an SV-NGEP polypeptide that can be used to express the SV-NGEP polypeptide (and thus be used to elicit an immune response against this polypeptide). For in vitro use, the immunogenic composition may consist of the isolated protein or peptide. For in vivo use, the immunogenic composition will typically comprise the protein or peptide in pharmaceutically acceptable carriers, and/or other agents. Any particular peptide, SV-NGEP polypeptide, or nucleic acid encoding the polypeptide, can be readily tested for its ability to induce a CTL or B cell response by art-recognized assays.

Isolated: An "isolated" biological component (such as a nucleic acid or protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule to facilitate detection of that molecule. Specific, non-limiting examples of labels include fluorescent tags, enzymatic linkages, and radioactive isotopes.

Lymphocytes: A type of white blood cell that is involved in the immune defenses of the body. There are two main types of lymphocytes: B cells and T cells.

Mammal: This term includes both human and non-human mammals. Similarly, the term "subject" includes both human and veterinary subjects.

Oligonucleotide: A linear polynucleotide sequence of up to about 100 nucleotide bases in length.

Open reading frame (ORF): A series of nucleotide triplets (codons) coding for amino acids without any internal termination codons. These sequences are usually translatable into a peptide.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence.

Generally, operably linked DNA sequences are contiguous and, where necessary to join two protein-coding regions, in the same reading frame.

Peptide: A chain of amino acids of between 3 and 30 amino acids in length. In one embodiment, a peptide is from about 10 to about 25 amino acids in length. In yet another embodiment, a peptide is from about 11 to about 20 amino acids in length. In yet another embodiment, a peptide is about 12 amino acids in length.

Peptide Modifications: SV-NGEP polypeptides include synthetic embodiments of peptides described herein. In addition, analogues (non-peptide organic molecules), derivatives (chemically functionalized peptide molecules obtained starting with the disclosed peptide sequences) and variants (homologs) of these proteins can be utilized in the methods described herein. Each polypeptide of this disclosure is comprised of a sequence of amino acids, which may be either L- and/or D-amino acids, naturally occurring and otherwise.

Peptides may be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides of this invention to select and provide conformational constraints to the structure that result in enhanced stability.

Peptidomimetic and organomimetic embodiments are envisioned, whereby the three-dimensional arrangement of the chemical constituents of such peptido- and organomimetics mimic the three-dimensional arrangement of the peptide backbone and component amino acid side chains, resulting in such peptido- and organomimetics of an SV-NGEP polypeptide having measurable or enhanced ability to generate an immune response. For computer modeling applications, a pharmacophore is an idealized three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs," in Klegerman & Groves, eds., 1993, *Pharmaceutical Biotechnology*, Interpharm Press: Buffalo Grove, Ill., pp. 165-174 and *Principles of Pharmacology* Munson (ed.) 1995, Ch. 102, for descriptions of techniques used in CADD. Also included are mimetics prepared using such techniques.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polynucleotide: The term polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

Polypeptide: Any chain of amino acids, regardless of length or post-translational modification (e.g., glycosylation or phosphorylation). In one embodiment, the polypeptide is SV-NGEP polypeptide.

Probes and primers: A probe comprises an isolated nucleic acid attached to a detectable label or reporter molecule. Primers are short nucleic acids, preferably DNA oligonucleotides, 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art. One of skill in the art will appreciate that the specificity of a particular probe or primer increases with its length. Thus, for example, a primer comprising 20 consecutive nucleotides will anneal to a target with a higher specificity than a corresponding primer of only 15 nucleotides. Thus, in order to obtain greater specificity, probes and primers may be selected that comprise 20, 25, 30, 35, 40, 50 or more consecutive nucleotides.

Promoter: A promoter is an array of nucleic acid control sequences that directs transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. Both constitutive and inducible promoters are included (see e.g., Bitter et al., *Methods in Enzymology* 153:516-544, 1987).

Specific, non-limiting examples of promoters include promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used. A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Protein Purification: The SV-NGEP polypeptides disclosed herein can be purified (and/or synthesized) by any of the means known in the art (see, e.g., *Guide to Protein Purification*, ed. Deutscher, *Meth. Enzymol.* 185, Academic Press, San Diego, 1990; and Scopes, *Protein Purification: Principles and Practice*, Springer Verlag, New York, 1982). Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components.

Purified: The term purified does not require absolute purity; rather, it is intended as a relative term. Thus, for example, a purified nucleic acid is one in which the nucleic acid is more enriched than the nucleic acid in its natural environment within a cell. Similarly, a purified peptide preparation is one in which the peptide or protein is more enriched than the peptide or protein is in its natural environment within a cell. In one embodiment, a preparation is purified such that the protein or peptide represents at least 50% (such as, but not limited to, 70%, 80%, 90%, 95%, 98% or 99%) of the total peptide or protein content of the preparation.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Selectively hybridize: Hybridization under moderately or highly stringent conditions that excludes non-related nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA versus DNA) of the hybridizing regions of the nucleic acids can be considered in selecting hybridization conditions. An additional consideration is whether one of the nucleic acids is immobilized, for example, on a filter.

A specific, non-limiting example of progressively higher stringency conditions is as follows: 2×SSC/0.1% SDS at about room temperature (hybridization conditions); 0.2× SSC/0.1% SDS at about room temperature (low stringency conditions); 0.2×SSC/0.1% SDS at about 42° C. (moderate stringency conditions); and 0.1×SSC at about 68° C. (high stringency conditions). One of skill in the art can readily determine variations on these conditions (e.g., *Molecular Cloning: A Laboratory Manual*, 2nd ed., vol. 1-3, ed. Sambrook et al., Cold Spring Harbor Laboratory Press, Cold Spring Harbor, N.Y., 1989). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of an SV-NGEP polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. USA* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. USA* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the Internet, for use in connection with the sequence analysis programs blastp, blastn, blastx, tblastn and tblastx. A description of how to determine sequence identity using this program is available on the NCBI website on the internet.

Homologs and variants of an SV-NGEP polypeptide are typically characterized by possession of at least 75%, for example at least 80%, sequence identity counted over the full length alignment with the amino acid sequence of SV-NGEP using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the Internet. One of skill in the art will appreciate that these sequence identity ranges are provided for guidance only; it is entirely possible that strongly significant homologs could be obtained that fall outside of the ranges provided.

Specific binding agent: An agent that binds substantially only to a defined target. Thus an SV-NGEP specific binding agent is an agent that binds substantially to an SV-NGEP polypeptide. In one embodiment, the specific binding agent is a monoclonal or polyclonal antibody that specifically binds SV-NGEP. In one specific, non-limiting example, the monoclonal or polyclonal antibody binds SV-NGEP, but not NGEP.

Subject: Living multi-cellular vertebrate organisms, a category that includes both human and veterinary subjects, including human and non-human mammals.

T Cell: A white blood cell critical to the immune response. T cells include, but are not limited to, CD4$^+$ T cells and CD8$^+$ T cells. A CD4$^+$ T lymphocyte is an immune cell that carries a marker on its surface known as "cluster of differentiation 4" (CD4). These cells, also known as helper T cells, help orchestrate the immune response, including antibody responses as well as killer T cell responses. CD8$^+$ T cells carry the "cluster of differentiation 8" (CD8) marker. In one embodiment, a CD8 T cell is a cytotoxic T lymphocytes. In another embodiment, a CD8 cell is a suppressor T cell.

Therapeutically active polypeptide: An agent, such as an SV-NGEP polypeptide that causes induction of an immune response, as measured by clinical response (for example increase in a population of immune cells, production of antibody that specifically binds SV-NGEP, or measurable reduction of tumor burden). Therapeutically active molecules can also be made from nucleic acids. Examples of a nucleic acid based therapeutically active molecule is a nucleic acid sequence that encodes an SV-NGEP polypeptide, wherein the nucleic acid sequence is operably linked to a control element such as a promoter. Therapeutically active agents can also include organic or other chemical compounds that mimic the effects of SV-NGEP.

The terms "therapeutically effective fragment of SV-NGEP" or "therapeutically effective variant of SV-NGEP" includes any fragment of SV-NGEP, or variant of SV-NGEP, that retains a function of SV-NGEP, or retains an antigenic epitope of SV-NGEP.

In one embodiment, a therapeutically effective amount of a fragment of SV-NGEP is an amount used to generate an immune response, or to treat prostate cancer in a subject. Specific, non-limiting examples are the N-terminal half of SV-NGEP or the C-terminal half of SV-NGEP. Treatment refers to a therapeutic intervention that ameliorates a sign or symptom of prostate cancer, or a reduction in tumor burden.

Transduced: A transduced cell is a cell into which has been introduced a nucleic acid molecule by molecular biology techniques. As used herein, the term transduction encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. "Comprise" means "include." It is further to be understood that all base sizes or amino acid sizes, and all molecular weight or molecular mass values, given for nucleic acids or polypeptides are approximate, and are provided for description. Although methods and materials similar or equivalents to those described herein can be used in the practice or testing of the present disclosure, suitable methods and materials are described below. In case of conflict, the present specification, including explanations of terms, will control. In addition, the materials, methods, and examples are illustrative only and not intended to be limiting.

SV-NGEP Polynucleotides and Polypeptides

Substantially purified SV-Novel Gene Expressed in Prostate (SV-NGEP) polypeptides are disclosed herein. In one embodiment, an SV-NGEP polypeptide has a sequence set forth as follows:

```
MRMAATAWAGLQGPPLPTLCPAVRTGLYCRDQAHAER   (SEQ ID NO:1)
WAMTSETSSGSHCARSRMLRRRAQEEDSTVLIDVSPP
EAEKRGSYGSTAHASEPGGQQAAACRAGSPAKPRIAD
FVLVWEEDLKLDRQQDSAARDRTDMHRTWRETFLDNL
RAAGLCVDQQDVQDGNTTVHYALLSASWAVLCYYAED
LRLKLPLQELPNQASNWSAGLLAWLGIPNVLLEVVPD
VPPEVVSCRFRVNKLPRFLGSDNQDTFFTSTKRHQIL
FEILAKTPYGHEKKNLLGIHQLLAEGVLSAAFPLHDG
PFKTPPEGPQAPRLNQRQVLFQHWARWGKWNKYQPLD
HVRRYFGEKVALYFAWLGFYTGWLLPAAVVGTLVFLV
GCFLVFSDIPTQELCGSKSFEMCPLCLDCPFWLLSSA
CALAQAGRLFDHGGTVFFSLFMALWAVLLLEYWKRKS
ATLAYRWDCSDYEDTEERPRPQFAASAPMTAPNPITG
EDEPYFPERSRARRMLAGSVVIVVMVAVVVMCLVSII
LYRAIMAIVVSRSGNTLLAAWASRIASLTGSVVNLVF
ILILSKIYVSLAHVLTRWEMHRTQTKFEDAFTLKVFI
FQFVNFYSSPVYIAFFKGRFVGYPGNYHTLFGVRNEE
CAAGGCLIELAQELLVIMVGKQVINNMQEVLIPKLKG
WWQKFRLRSKKRKAGASAGASQGPWEDDYELVPCEGL
FDEYLEMVLQFGFVTIFVAACPLAPLFALLNNWVEIR
LDARKFVCEYRRPVAERAQDIGIWFHILAGLTHLAVI
SNAFLLAFSSDFLPRAYYRWTRAHDLRGFLNFTLARA
PSSFAAAHNRTCRYRAFRDDDGHYSQTYWNLLAIRLA
FVIVFEHVVFSVGRLLDLLVPDIPESVEIKVKREYYL
AKQALAENEVLFGTNGTKDEQPKGSELSSHWTPFTVP
KASQLQQ
```

This polypeptide sequence is related to, but is not the same as, the Novel Gene Expressed in Prostate (NGEP) sequence shown in International Application No. PCT/US02/36648, filed on Nov. 13, 2002, which claims the benefit of U.S. Provisional Application No. 60/336,308, filed Nov. 14, 2001, both of which are incorporated by reference herein in their entirety. Specifically, SV-NGEP is 100% identical to NGEP from amino acid 1 to amino acid 157. However, the two amino acid sequences diverge from amino acid 158 to the end of the SV-NGEP sequence (amino acid 933).

In a second embodiment, an SV-NGEP polypeptide has a sequence at least 75%, 85%, 90%, 95%, 96%, 97%, 98% or 99% homologous to the amino acid sequence set forth in SEQ ID NO: 1. For example, the polypeptide can have an amino acid sequence, at least 85%, 90%, 95%, 96%, 97%, 98% or 99% homologous to the amino acid sequence set forth in SEQ ID NO: 1. Exemplary sequences can be obtained using computer programs that are readily available on the internet and the amino acid sequences set forth herein. In one example, the polypeptide retains a function of SV-NGEP, such as binding to an antibody that specifically binds an SV-NGEP epitope. In another embodiment, the polypeptide is expressed in prostate cancer.

In another embodiment, an SV-NGEP polypeptide has a sequence as set forth a SEQ ID NO: 1 or includes at most about five, ten, or twenty conservative substitutions of SEQ ID NO: 1. In one embodiment, these conservative substitutions are included in the region from amino acid 157 to the C-terminus of the polypeptide, such as to amino acid 933 of the full length SV-NGEP. Generally, the conservative variant will retain a function of SV-NGEP, such as binding to an antibody that specifically binds SV-NGEP, or being expressed in prostate cancer. In a further embodiment, an SV-NGEP polypeptide has a sequence as set forth as SEQ ID NO: 1.

Fragments of an SV-NGEP polypeptide can readily be prepared by one of skill in the art using molecular techniques. In one embodiment, a fragment of an SV-NGEP polypeptide includes at least 8, 10, 15, or 20 consecutive amino acids of an SV-NGEP polypeptide that are included in the amino acid sequence between about amino acid 150 and the C-terminus of SV-NGEP, such as between amino acid 157 and amino acid 933 of SEQ ID NO: 1. One of skill in the art can readily identify such fragments. Exemplary fragments include amino acids 158-166, 159-167, 160-168, 161-176, etc., or SEQ ID NO: 1, or amino acids 158-168, 159-169,160-170, 161-181, 162-182 of SEQ ID NO: 1, etc., of SEQ ID NO:1. Using basic mathematics, additional fragments can be identified.

SV-NGEP polypeptide sequences include, but are not limited to, the following SV-NGEP fragments:

| Amino Acid Position | Cellular Location of Fragment |
|---|---|
| 1-345 | cytoplasmic |
| 346-368 | transmembrane |
| 369-421 | External (cell surface) |
| 422-441 | transmembrane |
| 442-501 | cytoplasmic |
| 502-524 | transmembrane |
| 525-543 | External (cell surface) |
| 544-566 | transmembrane |
| 567-586 | cytoplasmic |
| 587-609 | transmembrane |
| 610-714 | External (cell surface) |
| 715-737 | transmembrane |
| 738-761 | Cytoplasmic |
| 762-784 | Transmembrane |
| 785-933 | External (cell surface) |

In another embodiment, an SV-NGEP polypeptide is a fragment of a full-length SV-NGEP polypeptide that includes a specific antigenic epitope found on full-length SV-NGEP. An antibody or an MHC molecule can specifically bind the antigenic epitope. In one embodiment, the SV-NGEP fragment is a polypeptide that specifically binds an antibody that binds full-length SV-NGEP. In one example, this antibody does not bind an epitope include in NGEP, which corresponds to amino acids 1-157 of SEQ ID NO: 1.

In several examples, SV-NGEP fragments include, but are not limited to, a polypeptide including at least 8 consecutive amino acids of the cytoplasmic region of SV-NGEP, such as at least 8 (e.g. 10, 15, 20, 25, etc.) consecutive amino acids of the sequence shown as amino acids 369-421 of SEQ ID NO: 1, amino acids 525-543 of SEQ ID NO: 1, amino acids 610-657 of SEQ ID NO: 1, or amino acids 738-761 of SEQ ID NO: 1. These fragments also include, a polypeptide including at least 8 consecutive amino acids of the external (cell-surface) region of SV-NGEP, such as, but not limited to 8 consecutive amino acids of the sequence shown as amino acids 369-421 of SEQ ID NO:1, amino acids 525-543 of SEQ ID NO:1, amino acids 610-714 of SEQ ID NO: 1, or amino acids 785-933 of SEQ ID NO: 1. In another embodiment, the fragment is a peptide, such as a 9- or a 10-mer that specifically binds an MHC molecule. In one specific non-limiting example, the fragment is a polypeptide including at least about 8 consecutive amino acids of the sequence set forth from about amino acid 875 to about amino acid 933 of SEQ ID NO: 1.

The presentation of peptides by MHC Class I molecules involves the cleavage of an endogenously produced protein into peptides by the proteasome, its processing through the ER and Golgi apparatus, its binding to the cleft in an MHC Class I molecule through the anchor residues of the peptide and ultimate presentation on the cell surface. Depending upon the particular anchor residues, among other things, certain peptides may bind more tightly to particular HLA molecules than others. Peptides that bind well are referred to as "dominant" epitopes, while those that bind less well are termed "subdominant" or "cryptic" epitopes. Dominant epitopes of either self proteins or foreign proteins evoke strong tolerance or immune responses. Subdominant or cryptic epitopes generate weak responses or no responses at all. Without being bound by theory, tighter binding by dominant epitopes to HLA molecules results in their denser presentation on the cell surface, greater opportunity to react with immune cells and greater likelihood of eliciting an immune response or tolerance. MHC Class I molecules present epitopes from endogenous proteins for presentation to $T_C$ cells. HLA A, HLA B and HLA C molecules bind peptides of about 8 to 10 amino acids in length that have particular anchoring residues. The anchoring residues recognized by an HLA Class I molecule depend upon the particular allelic form of the HLA molecule. A CD8+ T cell bears T cell receptors that recognize a specific epitope when presented by a particular HLA molecule on a cell. When a $T_C$ cell that has been stimulated by an antigen presenting cell to become a cytotoxic T lymphocyte contacts a cell that bears such an HLA-peptide complex, the CTL forms a conjugate with the cell and destroys it. Programs are available on the Internet for the prediction of epitopes that bind MHC.

For example, an HLA binding motif program on the Internet (Bioinformatics and Molecular Analysis Section-BIMAS) predicts the following 9-mers of SV-NGEP will bind HLA2-01:

| | |
|---|---|
| SLFMALWAV | (SEQ ID NO:3) |
| VLLEVVPDV | (SEQ ID NO:4) |
| ALLSASWAV | (SEQ ID NO:5) |
| LLAIRLAFV | (SEQ ID NO:6) |

```
            -continued
ILILSKIYV           (SEQ ID NO:7)

ILFEILAKT           (SEQ ID NO:8)

WLLSSACAL           (SEQ ID NO:9)

KIYVSLAHV           (SEQ ID NO:10)
```

Using the SV-NGEP amino acid sequence set forth as amino acids 158 to amino acid 933 of SEQ ID NO: 1, additional epitopes of interest can be identified using computer programs available on the internet. Thus, in one embodiment, a SV-NGEP fragment does not include about 8 consecutive amino acids of NGEP (amino acids 1-157 of SEQ ID NO: 1).

One skilled in the art, given the disclosure herein, can purify SV-NGEP polypeptide, or SV-NGEP 9-mers, or other fragments, using standard techniques for protein purification. The substantially pure polypeptide will yield a single major band on a non-reducing polyacrylamide gel. The purity of the SV-NGEP polypeptide can also be determined by amino-terminal amino acid sequence analysis.

Minor modifications of the SV-NGEP polypeptide primary amino acid sequences may result in peptides which have substantially equivalent activity as compared to the unmodified counterpart polypeptide described herein. Such modifications may be deliberate, as by site-directed mutagenesis, or may be spontaneous. All of the polypeptides produced by these modifications are included herein.

Thus, a specific, non-limiting example of an SV-NGEP polypeptide is a conservative variant of SV-NGEP. A table of conservative substitutions is provided herein. Substitutions of the amino acids sequence shown in SEQ ID NO: 1 can be made based on this table. Thus, one non-limiting example of a conservative variant is substitution of amino acid one (Met) of SEQ ID NO: 1 with an arginine residue. Similarly, another non-limiting example is substitution of amino acid 2 (Arg) of SEG ID NO: 1 with a lysine residue. Using the sequence provided as SEQ ID NO: 1, and the description of conservative amino acid substitutions provided, one of skill in the art can readily ascertain sequences of conservative variants. In several embodiments, a conservative variant includes at most one, at most two, at most five, at most ten, or at most fifteen conservative substitutions of the sequence shown in SEQ ID NO: 1. Generally, a conservative variant will bind to antibodies that immunoreact with (specifically bind to) a polypeptide having a sequence set forth as SEQ ID NO: 1. In several examples, a conservative variant includes at most two, at most five, at most eight, at most ten, or at most fifteen conservative substitutions of SEQ ID NO: 1, wherein the conservative variant retains a function of SV-NGEP.

One of skill in the art can readily produce fusion proteins including an SV-NGEP polypeptide and a second polypeptide of interest. Optionally, a linker can be included between the SV-NGEP polypeptide and the second polypeptide of interest. Fusion proteins include, but are not limited to, a polypeptide including an SV-NGEP polypeptide and a marker protein. In one embodiment, the marker protein can be used to identify or purify an SV-NGEP polypeptide. Exemplary fusion proteins included, but are not limited, to green fluorescent protein, six histidine residues, or myc and an SV-NGEP polypeptide.

Polynucleotides encoding an SV-NGEP polypeptide are also provided, and are termed SV-NGEP polynucleotides. These polynucleotides include DNA, cDNA and RNA sequences which encode SV-NGEP. It is understood that all polynucleotides encoding an SV-NGEP polypeptide are also included herein, as long as they encode a polypeptide with the recognized activity, such as the binding to an antibody that recognizes an SV-NGEP polypeptide. The polynucleotides of this disclosure include sequences that are degenerate as a result of the genetic code. There are 20 natural amino acids, most of which are specified by more than one codon. Therefore, all degenerate nucleotide sequences are included in the invention as long as the amino acid sequence of the SV-NGEP polypeptide encoded by the nucleotide sequence is functionally unchanged. One specific, non-limiting example of a polynucleotide encoding SV-NGEP is

```
aaaagatagatcctgctccaggagccgggaagcctcg  (SEQ ID NO:2)

ccctggccagctgtgctgggcacctccctgcctgct tcctggcccacttgcaggcaaggtgagggcATGCGAA

TGGCTGCCACTGCCTGGGCGGGGCTCCAAGGGCCACC

CCTCCCCACCCTCTGTCCCGCAGTGAGGACGGGACT

CTACTGCCGAGACCAGGCTCACGCTGAGAGGTGGGCC

ATGACCTCCGAGACCTCTTCCGGAAGCCACTGTGCCA

GGAGCAGGATGCTGCGGCGACGGGCCCAGGAAGAGGA

CAGCACCGTCCTGATCGATGTGAGCCCCCCTGAGGCA

GAGAAGAGGGGCTCTTACGGGAGCACAGCCCACGCCT

CGGAGCCAGGTGGACAGCAAGCGGCCGCCTGCAGAGC

TGGGAGTCCTGCCAAGCCCCGGATCGCAGACTTCGTC

CTCGTTTGGGAGGAGGACCTGAAGCTAGACAGGCAGC

AGGACAGTGCCGCCCGGGACAGAACAGACATGCACAG

GACCTGGCGGGAGACTTTTCTGGATAATCTTCGTGCG

GCTGGGCTGTGTGTAGACCAGCAGGACGTCCAGGACG

GGAACACCACAGTGCACTACGCCCTCCTCAGCGCCTC

CTGGGCTGTGCTCTGCTACTACGCCGAAGACCTGCGC

CTGAAGCTGCCCTTGCAGGAGTTACCCAACCAGGCCT

CCAACTGGTCGGCCGGCCTGCTGGCATGGCTGGGCAT

CCCCAACGTCCTGCTGGAGGTTGTGCCAGACGTACCC

CCCGAGTACTACTCCTGCCGGTTCAGAGTGAACAAGC

TGCCACGCTTCCTCGGGAGTGACAACCAGGACACCTT

CTTCACAAGCACCAAGAGGCACCAAATTCTGTTTGAG

ATCCTGGCCAAGACCCCGTATGGCCACGAGAAGAAAA

ACCTGCTTGGGATCCACCAGCTGCTGGCAGAGGGTGT

CCTCAGTGCCGCCTTCCCCCTGCATGACGGCCCCTTC

AAGACGCCCCAGAGGGCCCGCAGGCTCCACGCCTCA

ACCAGCGCCAAGTCCTTTTCCAGCACTGGGCGCGCTG

GGGCAAGTGGAACAAGTACCAGCCCCTGGACCACGTG

CGCAGGTACTTCGGGGAGAAGGTGGCCCTCTACTTCG

CCTGGCTCGGGTTTTACACAGGCTGGCTCCTGCCAGC

GGCAGTGGTGGGCACACTGGTGTTCCTGGTGGGCTGC
```

```
-continued
TTCCTGGTGTTCTCAGACATACCCACGCAGGAACTGT

GTGGCAGCAAGGACAGCTTCGAGATGTGCCCACTTTG

CCTCGACTGCCCTTTCTGGCTGCTCTCCAGCGCCTGT

GCCCTGGCCCAGGCCGGCCGGCTGTTCGACCACGGCG

GCACCGTGTTCTTCAGCTTGTTCATGGCACTGTGGGC

CGTGCTGCTGCTGGAGTACTGGAAGCGGAAGAGCGCC

ACGCTGGCCTACCGCTGGGACTGCTCTGACTACGAGG

ACACTGAGGAGAGGCCTCGGCCCCAGTTTGCCGCCTC

AGCCCCCATGACAGCCCCGAACCCCATCACGGGTGAG

GACGAGCCCTACTTCCCTGAGAGGAGCCGCGCGCGCC

GCATGCTGGCCGGCTCTGTGGTGATCGTGGTGATGGT

GGCCGTGGTGGTCATGTGCCTCGTGTCTATCATCCTG

TACCGTGCCATCATGGCCATCGTGGTGTCCAGGTCGG

GCAACACCCTTCTCGCAGCCTGGGCCTCTCGCATCGC

CAGCCTCACGGGGTCTGTAGTGAACCTCGTCTTCATC

CTCATCCTCTCCAAGATCTATGTATCCCTGGCCCACG

TCCTGACACGATGGGAAATGCACCGCACCCAGACCAA

GTTCGAGGACGCCTTCACCCTCAAGGTGTTCATCTTC

CAGTTCGTCAACTTCTACTCCTCACCCGTCTACATTG

CCTTCTTCAAGGGCAGGTTTGTGGGATACCCAGGCAA

CTACCACACCTTGTTTGGAGTCCGCAATGAGGAGTGC

GCGGCTGGAGGCTGCCTGATCGAGCTGGCACAGGAGC

TCCTGGTCATCATGGTGGGCAAGCAGGTCATCAACAA

CATGCAGGAGGTCCTCATCCCGAAGCTAAAGGGCTGG

TGGCAGAAGTTCCGGCTTCGCTCCAAGAAGAGGAAGG

CGGGAGCTTCTGCAGGGGCTAGCCAGGGGCCCTGGGA

GGACGACTATGAGCTTGTGCCCTGTGAGGGTCTGTTT

GACGAGTACCTGGAAATGGTGCTGCAGTTCGGCTTCG

TCACCATCTTCGTGGCCGCCTGTCCGCTCGCGCCGCT

CTTCGCCCTGCTCAACAACTGGGTGGAGATCCGCTTG

GACGCGCGCAAGTTCGTCTGCGAGTACCGGCGCCCTG

TGGCCGAGCGCGCCCAGGACATCGGCATCTGGTTCCA

CATCCTGGCGGGCCTCACGCACCTGGCGGTCATCAGC

AACGCCTTCCTCCTGGCCTTCTCGTCCGACTTCCTGC

CGCGCGCCTACTACCGGTGGACCCGCGCCCACGACCT

GCGCGGCTTCCTCAACTTCACGCTGGCGCGAGCCCCG

TCCTCCTTCGCCGCCGCGCACAACCGCACGTGCAGGT

ATCGGGCTTTCCGGGATGACGATGGACATTATTCCCA

GACCTACTGGAATCTTCTTGCCATCCGCCTGGCCTTC

GTCATTGTGTTTGAGCATGTGGTTTTCTCCGTTGGCC
```

```
-continued
GCCTCCTGGACCTCCTGGTGCCTGACATCCCAGAGTC

TGTGGAGATCAAAGTGAAGCGGGAGTACTACCTGGCT

AAGCAGGCACTGGCTGAGAATGAGGTTCTTTTTGGAA

CGAACGGAACAAAGGATGAGCAGCCCAAGGGCTCAGA

GCTCAGCTCCCACTGGACACCCTTCACGGTTCCCAAG

GCCAGCCAGCTGCAGCAGTGAcgcctggaaggacatc tggtggtccttaggggagtggccctcctgagccctg cgagcagcgtcctttcctcttccctcaggcagcggc tgtgtgaaccgctggctgctgttgtgcctcatctctg ggcacattgcctgcttcccccagcgccggcttctct cctcagagcgcctgtcactccatccccggcagggagg gaccgtcagctcacaaggccctctttgtttcctgctc ccagacataagcccaaggggccctgcacccaaggga ccctgtccctcggtggcctcccaggccctggacac gacagttctcctcaggcaggtgggctttgtggtcctc gccgccctggccacatcgccctctcctcttacacct ggtgaccttcgaatgt
```

This polynucleotide sequence is related to the polynucleotide sequence shown in International Application No. PCT/US02/36648, filed on Nov. 13, 2002, which claims the benefit of U.S. Provisional Application No. 60/336,308, filed Nov. 14, 2001, both of which are incorporated by reference herein in their entirety.

Another specific non-limiting example of a polynucleotide encoding SV-NGEP is a polynucleotide having at least 75%, 85%, 90%, 95%, or 99% homologous to SEQ ID NO: 2 that encodes a polypeptide having an antigenic epitope or function of SV-NGEP. Yet another specific non-limiting example of a polynucleotide encoding SV-NGEP is a polynucleotide that encodes a polypeptide that is specifically bound by an antibody that specifically binds SEQ ID NO: 1. This antibody can specifically bind an antigenic epitope, such as an antigenic epitope included in amino acids 158 to amino acids 933 of SEQ ID NO: 1. In one example, the epitope is not included in amino acids 1-157 of SEQ ID NO: 1. In additional embodiments, the polynucleotide includes at least ten, at least 15, at least 20, at least 30, or at least 40 nucleotides of a polynucleotide that encodes amino acid 158 to 933 of SV-NGEP (SEQ ID NO: 1).

Primers, such as PCR primers can readily be prepared from an SV-NGEP polynucleotide. In one embodiment, the primers include at least ten, at least 15, 16, 17, 18, 18, or 20 consecutive nucleotides of SEQ ID NO: 2. Also included are fragments of the above-described nucleic acid sequences that are at least 15 bases in length, which is sufficient to permit the fragment to selectively hybridize to DNA that encodes the disclosed SV-NGEP polypeptide (e.g. a polynucleotide that encodes SEQ ID NO: 1) under physiological conditions. In one example, an SV-NGEP polynucleotide is a polynucleotides that includes at least 8 consecutive nucleotides (such as at least ten, at least 15, 16, 17, 18, 18, or 20 consecutive nucleotides) of a polynucleotide that encodes amino acids 158-933 of SEQ ID NO: 1. In one embodiment, these fragments can be used to differentiate a nucleic acid that encodes NGEP (amino acids 1-157 of SEQ ID NO: 1) from a nucleic acid that encodes SV-NGEP (SEQ ID NO: 1). The term "selectively hybridize" refers to hybridization under moderately or highly stringent conditions, which excludes non-related nucleotide sequences.

A nucleic acid encoding SV-NGEP can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the protein can be isolated by polymerase chain reaction of cDNA using primers based on the DNA sequence of the molecule. A wide variety of cloning and in vitro amplification methodologies are well known to persons skilled in the art. PCR methods are described in, for example, U.S. Pat. No. 4,683,195; Mullis et al. (1987) Cold Spring Harbor Symp. Quant. Biol. 51:263; and Erlich, ed., PCR Technology, (Stockton Press, N.Y., 1989). Polynucleotides also can be isolated by screening genomic or cDNA libraries with probes selected from the sequences of the desired polynucleotide under stringent hybridization conditions.

The SV-NGEP polynucleotides include a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides of the invention can be ribonucleotides, deoxyribonucleotides, or modified forms of either nucleotide. The term includes single and double forms of DNA. The SV-NGEP polynucleotide sequence disclosed herein include, but are not limited to, SEQ ID NO: 2, degenerate variants of SEQ ID NO: 2, and sequences that encode conservative variations of SV-NGEP polypeptide.

DNA sequences encoding SV-NGEP polypeptide can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

SV-NGEP polynucleotide sequences can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

The polynucleotide sequences encoding SV-NGEP may be inserted into an expression vector including, but not limited to, a plasmid, virus or other vehicle that can be manipulated to allow insertion or incorporation of sequences and can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art.

Transformation of a host cell with recombinant DNA may be carried out by conventional techniques as are well known to those skilled in the art. Where the host is prokaryotic, such as E. coli, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with SV-NGEP polynucleotide sequences, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Eukaryotic Viral Vectors, Cold Spring Harbor Laboratory, Gluzman ed., 1982).

Isolation and purification of recombinantly expressed polypeptides may be carried out by conventional means including preparative chromatography and immunological separations.

Antibodies

An SV-NGEP polypeptide or a fragment or conservative variant thereof can be used to produce antibodies which are immunoreactive or bind to an epitope of SV-NGEP. Polyclonal antibodies, antibodies which consist essentially of pooled monoclonal antibodies with different epitopic specificities, as well as distinct monoclonal antibody preparations are included.

In one embodiment, the antibody that specifically binds SV-NGEP does not bind NGEP (see U.S. Provisional Application No. PCT/US02/36648, filed on Nov. 13, 2002, which claims the benefit of International Application No. 60/336,308, filed Nov. 14, 2001, both of which are incorporated by reference herein in their entirety). Thus, in a specific, non-limiting example, the antibody specifically binds an antigenic epitope of SV-NGEP that is not an antigenic epitope of NGEP. In one example, the antibody specifically binds an antigenic epitope that includes at least six consecutive amino acids from amino acid 157 to the C-terminus of SV-NGEP. Suitable antigenic epitopes are disclosed herein. In one embodiment, the antibody binds an extracellular domain of SV-NGEP (see Table above for the location of extracellular domains). For example, the antibody can bind an antigenic epitope included in the extracellular domain located from about amino acid 875 to about amino acid 933 of SV-NGEP.

In another embodiment, the antibody that specifically binds SV-NGEP also binds NGEP. Thus, in a specific, non-limiting example, the antibody specifically binds an antigenic epitope that is found in both SV-NGEP and NGEP.

The preparation of polyclonal antibodies is well known to those skilled in the art. See, for example, Green et al., "Production of Polyclonal Antisera, in: Immunochemical Protocols pages 1-5, Manson, ed., Humana Press 1992; Coligan et al., "Production of Polyclonal Antisera in Rabbits, Rats, Mice and Hamsters, in: Current Protocols in Immunology, section 2.4.1, 1992.

The preparation of monoclonal antibodies likewise is conventional. See, for example, Kohler & Milstein, Nature 256: 495, 1975; Coligan et al., sections 2.5.1-2.6.7; and Harlow et al., in: Antibodies: a Laboratory Manual, page 726, Cold Spring Harbor Pub., 1988. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1-2.7.12 and sections 2.9.1-2.9.3; Barnes et al., "Purification of Immunoglobulin G (IgG)," in: *Methods in Molecular Biology*, Vol. 10, pages 79-104, Humana Press, 1992.

Methods of in vitro and in vivo multiplication of monoclonal antibodies are well known to those skilled in the art. Multiplication in vitro may be carried out in suitable culture media such as Dulbecco's Modified Eagle Medium or RPMI 1640 medium, optionally supplemented by a mammalian serum such as fetal calf serum or trace elements and growth-sustaining supplements such as normal mouse peritoneal exudate cells, spleen cells, thymocytes or bone marrow macrophages. Production in vitro provides relatively pure antibody preparations and allows scale-up to yield large amounts of the desired antibodies. Large-scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Antibodies can also be derived from a subhuman primate antibody. General techniques for raising therapeutically useful antibodies in baboons can be found, for example, in WO 91/11465, 1991, and Losman et al., *Int. J. Cancer* 46:310, 1990.

Alternatively, an antibody that specifically binds an SV-NGEP polypeptide can be derived from a humanized monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA* 86:3833, 1989. Techniques for producing humanized monoclonal antibodies are described, for example, by Jones et al., *Nature* 321:522, 1986; Riechmann et al., *Nature* 332:323, 1988; Verhoeyen et al., *Science* 239:1534, 1988; Carter et al., *Proc. Nat'l Acad. Sci. USA* 89:4285, 1992; Sandhu, *Crit. Rev. Biotech.* 12:437, 1992; and Singer et al., *J. Immunol.* 150: 2844, 1993.

Antibodies can be derived from human antibody fragments isolated from a combinatorial immunoglobulin library. See, for example, Barbas et al., in: *Methods: a Companion to Methods in Enzymology*, Vol. 2, page 119, 1991; Winter et al., *Ann. Rev. Immunol.* 12:433, 1994. Cloning and expression vectors that are useful for producing a human immunoglobulin phage library can be obtained, for example, from STRATAGENE Cloning Systems (La Jolla, Calif.).

In addition, antibodies can be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13, 1994; Lonberg et al., *Nature* 368:856, 1994; and Taylor et al., *Int. Immunol.* 6:579, 1994.

Antibodies include intact molecules as well as fragments thereof, such as Fab, F(ab')$_2$, and Fv which are capable of binding the epitopic determinant. These antibody fragments retain some ability to selectively bind with their antigen or receptor and are defined as follows:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody (SCA), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, *Antibodies: A Laboratory Manual*, Cold Spring Harbor Laboratory, New York, 1988). An epitope is any antigenic determinant on an antigen to which the paratope of an antibody binds. Epitopic determinants usually consist of chemically active surface groupings of molecules such as amino acids or sugar side chains, and usually have specific three-dimensional structural characteristics, as well as specific charge characteristics.

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647, and references contained therein; Nisonhoff et al., *Arch. Biochem. Biophys.* 89:230, 1960; Porter, *Bio-* chem. J. 73:119, 1959; Edelman et al., *Methods in Enzymology*, Vol. 1, page 422, Academic Press, 1967; and Coligan et al., supra at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent (Inbar et al., *Proc. Nat'l Acad. Sci. USA* 69:2659, 1972). Alternatively, the variable chains can be linked by an intermolecular disulfide bond or cross-linked by chemicals such as glutaraldehyde. See, e.g., Sandhu, supra. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are known in the art (see Whitlow et al., *Methods: a Companion to Methods in Enzymology*, Vol. 2, page 97, 1991; Bird et al., *Science* 242:423, 1988; U.S. Pat. No. 4,946,778; Pack et al., *Bio/Technology* 11:1271, 1993; and Sandhu, supra).

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (Larrick et al., *Methods: a Companion to Methods in Enzymology*, Vol. 2, page 106, 1991).

Antibodies can be prepared using an intact polypeptide or fragments containing small peptides of interest as the immunizing antigen. The polypeptide or a peptide used to immunize an animal can be derived from substantially purified polypeptide produced in host cells, in vitro translated cDNA, or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

Polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan et al., Unit 9, *Current Protocols in Immunology*, Wiley Interscience, 1991).

It is also possible to use the anti-idiotype technology to produce monoclonal antibodies which mimic an epitope. For example, an anti-idiotypic monoclonal antibody made to a first monoclonal antibody will have a binding domain in the hypervariable region that is the "image" of the epitope bound by the first mono-clonal antibody.

Binding affinity for a target antigen is typically measured or determined by standard antibody-antigen assays, such as competitive assays, saturation assays, or immunoassays such as ELISA or RIA. Such assays can be used to determine the dissociation constant of the antibody. The phrase "dissociation constant" refers to the affinity of an antibody for an antigen. Specificity of binding between an antibody and an antigen exists if the dissociation constant ($K_D=1/K$, where K is the affinity constant) of the antibody is, for example <1 µM, <100 nM, or <0.1 nM. Antibody molecules will typically have a $K_D$ in the lower ranges. $K_D$=[Ab–Ag]/[Ab][Ag] where [Ab] is the concentration at equilibrium of the antibody, [Ag] is the concentration at equilibrium of the antigen and [Ab–Ag] is the concentration at equilibrium of the antibody-antigen complex. Typically, the binding interactions between antigen and antibody include reversible noncovalent associations such as electrostatic attraction, Van der Waals forces and hydrogen bonds.

Effector molecules, e.g., therapeutic, diagnostic, or detection moieties can be linked to an antibody that specifically binds SV-NGEP, using any number of means known to those of skill in the art. Exemplary effector molecules include, but not limited to, a radiolabels, fluorescent markers, or toxins (e.g. *Pseudomonas* exotoxin (PE), see "Monoclonal Antibody-Toxin Conjugates: Aiming the Magic Bullet," Thorpe et al., "Monoclonal Antibodies in Clinical Medicine", Academic Press, pp. 168-190, 1982; Waldmann, *Science*, 252: 1657, 1991; U.S. Pat. No. 4,545,985 and U.S. Pat. No. 4,894, 443, for a discussion of toxins and conjugation). Both covalent and noncovalent attachment means may be used. The procedure for attaching an effector molecule to an antibody varies according to the chemical structure of the effector. Polypeptides typically contain variety of functional groups; e.g., carboxylic acid (COOH), free amine (—$NH_2$) or sulfhydryl (—SH) groups, which are available for reaction with a suitable functional group on an antibody to result in the binding of the effector molecule. Alternatively, the antibody is derivatized to expose or attach additional reactive functional groups. The derivatization may involve attachment of any of a number of linker molecules such as those available from Pierce Chemical Company, Rockford, Ill. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (e.g., through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

In view of the large number of methods that have been reported for attaching a variety of radiodiagnostic compounds, radiotherapeutic compounds, label (e.g. enzymes or fluorescent molecules) drugs, toxins, and other agents to antibodies one skilled in the art will be able to determine a suitable method for attaching a given agent to an antibody or other polypeptide.

Therapeutic Methods and Pharmaceutical Compositions

An SV-NGEP polypeptide can be administered to a subject in order to generate an immune response. In one embodiment, a therapeutically effective amount of an SV-NGEP polypeptide is administered to a subject to treat prostate cancer.

In exemplary applications, compositions are administered to a patient suffering from a disease, such as prostate cancer, in an amount sufficient to raise an immune response to SV-NGEP-expressing cells. Administration induces a sufficient immune response to slow the proliferation of such cells or to inhibit their growth. Amounts effective for this use will depend upon the severity of the disease, the general state of the patient's health, and the robustness of the patient's immune system. A therapeutically effective amount of the compound is that which provides either subjective relief of a symptom(s) or an objectively identifiable improvement as noted by the clinician or other qualified observer. In one example the polypeptide is an SV-NGEP polypeptide that does not include amino acid sequence set forth as amino acids 1-157 of SEQ ID NO: 1. In another example, the polypeptide does not include an amino acid sequence including at least about 8, at least about 10, at least about 15 or at least about 20 consecutive amino acids of the sequence set forth as amino acids 1-157 of SEQ ID NO: 1.

An SV-NGEP polypeptide can be administered by any means known to one of skill in the art (see Banga, A., Parenteral Controlled Delivery of Therapeutic Peptides and Proteins, in *Therapeutic Peptides and Proteins*, Technomic Publishing Co., Inc., Lancaster, Pa., 1995) such as by intramuscluar, subcutaneous, or intravenous injection, but even oral, nasal, or anal administration is contemplated. In one embodiment, administration is by subcutaneous or intramuscular injection. To extend the time during which the peptide or protein is available to stimulate a response, the peptide or protein can be provided as an implant, an oily injection, or as a particulate system. The particulate system can be a microparticle, a microcapsule, a microsphere, a nanocapsule, or similar particle. (see, e.g., Banja, supra). A particulate carrier based on a synthetic polymer has been shown to act as an adjuvant to enhance the immune response, in addition to providing a controlled release. Aluminum salts may also be used as adjuvants to produce a humoral immune response. Thus, in one embodiment, an SV-NGEP polypeptide is administered in a manner to induce a humoral response.

In another embodiment, an SV-NGEP polypeptide is administered in a manner to direct the immune response to a cellular response (that is, a CTL response), rather than a humoral (antibody) response. A number of means for inducing cellular responses, both in vitro and in vivo, are known. Lipids have been identified as agents capable of assisting in priming CTL in vivo against various antigens. For example, as described in U.S. Pat. No. 5,662,907, palmitic acid residues can be attached to the alpha and epsilon amino groups of a lysine residue and then linked (e.g., via one or more linking residues, such as glycine, glycine-glycine, serine, serine-serine, or the like) to an immunogenic peptide. The lipidated peptide can then be injected directly in a micellar form, incorporated in a liposome, or emulsified in an adjuvant. As another example, *E. coli* lipoproteins, such as tripalmitoyl-S-glycerylcysteinlyseryl-serine can be used to prime tumor specific CTL when covalently attached to an appropriate peptide (see, Deres et al., *Nature* 342:561, 1989). Further, as the induction of neutralizing antibodies can also be primed with the same molecule conjugated to a peptide which displays an appropriate epitope, the two compositions can be combined to elicit both humoral and cell-mediated responses where that is deemed desirable.

In yet another embodiment, to induce a CTL response to an immunogenic SV-NGEP polypeptide or fragment thereof, a MHC Class II-restricted T-helper epitope is added to the CTL antigenic peptide to induce T-helper cells to secrete cytokines in the microenvironment to activate CTL precursor cells. The technique further involves adding short lipid molecules to retain the construct at the site of the injection for several days to localize the antigen at the site of the injection and enhance its proximity to dendritic cells or other "professional" antigen presenting cells over a period of time (see Chesnut et al., "Design and Testing of Peptide-Based Cytotoxic T-Cell-Mediated Imunotherapeutics to Treat Infectious Diseases and Cancer," in Powell et al., eds., *Vaccine Design, the Subunit and Adjuvant Approach*, Plenum Press, New York, 1995).

A pharmaceutical composition including an SV-NGEP polypeptide is thus provided. In one embodiment, the SV-NGEP polypeptide, or fragment thereof, is mixed with an adjuvant containing two or more of a stabilizing detergent, a micelle-forming agent, and an oil. Suitable stabilizing detergents, micelle-forming agents, and oils are detailed in U.S. Pat. No. 5,585,103; U.S. Pat. No. 5,709,860; U.S. Pat. No. 5,270,202; and U.S. Pat. No. 5,695,770, all of which are incorporated by reference. A stabilizing detergent is any detergent that allows the components of the emulsion to remain as a stable emulsion. Such detergents include polysorbate, 80 (TWEEN) (Sorbitan-mono-9-octadecenoate-poly (oxy-1,2-ethanediyl; manufactured by ICI Americas, Wilmington, Del.), TWEEN 40™, TWEEN 20™, TWEEN 60™, Zwittergent™ 3-12, TEEPOL HB7™, and SPAN 85™. These detergents are usually provided in an amount of approximately 0.05 to 0.5%, preferably at about 0.2%. A micelle forming agent is an agent which is able to stabilize the emulsion formed with the other components such that a micelle-like structure is formed. Such agents generally cause some irritation at the site of injection in order to recruit macrophages to enhance the cellular response. Examples of such agents include polymer surfactants described by BASF Wyandotte publications, e.g., Schmolka, *J. Am. Oil. Chem. Soc.* 54:110, 1977, and Hunter et al., *J. Immunol* 129:1244, 1981, PLURONIC™ L62LF, L101, and L64, PEG1000, and TETRONIC™ 1501, 150R1, 701, 901, 1301, and 130R1. The chemical structures of such agents are well known in the art. In one embodiment, the agent is chosen to have a hydrophile-lipophile balance (HLB) of between 0 and 2, as defined by Hunter and Bennett, *J. Immun.* 133:3167, 1984. The agent can be provided in an effective amount, for example between 0.5 and 10%, most preferably in an amount between 1.25 and 5%.

The oil included in the composition is chosen to promote the retention of the antigen in oil-in-water emulsion, i.e., to provide a vehicle for the desired antigen, and preferably has a melting temperature of less than 65° C. such that emulsion is formed either at room temperature (about 20° C. to 25° C.), or once the temperature of the emulsion is brought down to room temperature. Examples of such oils include squalene, Squalane, EICOSANE™, tetratetracontane, glycerol, and peanut oil or other vegetable oils. In one specific, non-limiting example, the oil is provided in an amount between 1 and 10%, most preferably between 2.5 and 5%. The oil should be both biodegradable and biocompatible so that the body can break down the oil over time, and so that no adverse affects, such as granulomas, are evident upon use of the oil.

An adjuvant can be included in the composition. In one embodiment, the adjuvant is a mixture of stabilizing detergents, micelle-forming agent, and oil available under the name Provax® (IDEC Pharmaceuticals, San Diego, Calif.).

In another embodiment, a pharmaceutical composition includes a nucleic acid encoding an SV-NGEP polypeptide or immunogenic fragment thereof. A therapeutically effective amount of the SV-NGEP polynucleotide can be administered to a subject in order to generate an immune response. In one specific, non-limiting example, a therapeutically effective amount of the SV-NGEP polynucleotide is administered to a subject to treat prostate cancer.

One approach to administration of nucleic acids is direct immunization with plasmid DNA, such as with a mammalian expression plasmid. As described above, the nucleotide sequence encoding SV-NGEP, or an immunogenic peptide thereof, can be placed under the control of a promoter to increase expression of the molecule.

Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. No. 5,593,972 and U.S. Pat. No. 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and Quil A™ (saponin). Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as 1 µg encapsulated in ISCOMS™ have been found to produce Class I mediated CTL responses (Takahashi et al., *Nature* 344:873, 1990).

In another approach to using nucleic acids for immunization, an SV-NGEP polypeptide or an immunogenic peptide thereof can also be expressed by attenuated viral hosts or vectors or bacterial vectors. Recombinant *vaccinia* virus, adeno-associated virus (AAV), herpes virus, retrovirus, or other viral vectors can be used to express the peptide or protein, thereby eliciting a CTL response. For example, *vaccinia* vectors and methods useful in immunization protocols are described in U.S. Pat. No. 4,722,848. BCG (*Bacillus Calmette Guerin*) provides another vector for expression of the peptides (see Stover, *Nature* 351:456-460, 1991).

In one embodiment, a nucleic acid encoding an SV-NGEP polypeptide or an immunogenic fragment thereof is introduced directly into cells. For example, the nucleic acid may be loaded onto gold microspheres by standard methods and introduced into the skin by a device such as Bio-Rad's Helios™ Gene Gun. The nucleic acids can be "naked," consisting of plasmids under control of a strong promoter. Typically, the DNA is injected into muscle, although it can also be injected directly into other sites, including tissues in proximity to metastases. Dosages for injection are usually around 0.5 µg/kg to about 50 mg/kg, and typically are about 0.005 mg/kg to about 5 mg/kg (see, e.g., U.S. Pat. No. 5,589,466).

In addition, the cell growth inhibiting chimeric molecules including an antibody that specifically binds SV-NGEP linked to a toxin (such as, but not limited to, PE linked to an anti-SV-NGEP antibody), can be prepared in pharmaceutical compositions. These cell growth inhibiting molecules can be administered to a subject by any method known to one of skill in the art. For example, to treat prostate cancer, the pharmaceutical compositions of this disclosure can be administered directly into the prostate gland. Metastases of prostate cancer may be treated by intravenous administration or by localized delivery to the tissue surrounding the tumor.

The compositions for administration will commonly comprise a solution of the cell growth inhibiting chimeric molecules dissolved in a pharmaceutically acceptable carrier, preferably an aqueous carrier. A variety of aqueous carriers can be used, e.g., buffered saline and the like. These solutions are sterile and generally free of undesirable matter. These compositions can be sterilized by conventional, well-known sterilization techniques. The compositions can contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of cell growth inhibiting molecules in these formulations can vary, and will be selected primarily based on fluid volumes, viscosities, body weight and the like in accordance with the particular mode of administration selected and the patient's needs.

In one specific, non-limiting example, a pharmaceutical composition for intravenous administration, such as an immunotoxin, would be about 0.1 to 10 mg per patient per day. Dosages from 0.1 up to about 100 mg per patient per day can be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remingtons Phamaceutical Sciences*, $19^{th}$ Ed., Mack Publishing Company, Easton, Pa. (1995).

The compositions can be administered for therapeutic treatments. In therapeutic applications, a therapeutically effective amount of the composition is administered to a subject suffering from a disease, such as prostate cancer. Single or multiple administrations of the compositions are administered depending on the dosage and frequency as required and tolerated by the subject. In one embodiment, the dosage is administered once as a bolus, but in another embodiment can be applied periodically until either a therapeutic result is achieved. Generally, the dose is sufficient to treat or ameliorate symptoms or signs of disease without producing unacceptable toxicity to the subject. Systemic or local administration can be utilized.

Controlled release parenteral formulations of cell growth inhibiting chimeric molecules can be made as implants, oily injections, or as particulate systems. For a broad overview of protein delivery systems (see Banga, *Therapeutic Peptides and Proteins: Formulation, Processing, and Delivery Systems*, Technomic Publishing Company, Inc., Lancaster, Pa., 1995). Particulate systems include microspheres, microparticles, microcapsules, nanocapsules, nanospheres, and nanoparticles. Microcapsules contain the therapeutic protein as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly (see Kreuter, *Colloidal Drug Delivery Systems*, J. Kreuter, ed., Marcel Dekker, Inc., New York, N.Y., pp. 219-342, 1994; Tice & Tabibi,

*Treatise on Controlled Drug Delivery*, A. Kydonieus, ed., Marcel Dekker, Inc. New York, N.Y., pp. 315-339, 1992).

Polymers can be used for ion-controlled release. Various degradable and nondegradable polymeric matrices for use in controlled drug delivery are known in the art (Langer, *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992); and Pec, *J. Parent. Sci. Tech.* 44(2):58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa., 1993). Numerous additional systems for controlled delivery of therapeutic proteins are known (e.g., U.S. Pat. No. 5,055,303; U.S. Pat. No. 5,188,837; U.S. Pat. No. 4,235,871; U.S. Pat. No. 4,501,728; U.S. Pat. No. 4,837,028; U.S. Pat. No. 4,957,735; and U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206, U.S. Pat. No. 5,271,961; U.S. Pat. No. 5,254,342 and U.S. Pat. No. 5,534,496).

In another method, antigen presenting cells (APCs) are pulsed or co-incubated with peptides comprising an epitope from SV-NGEP in vitro. These cells are used to sensitize CD8 cells, such as tumor infiltrating lymphocytes from prostate cancer tumors or peripheral blood lymphocytes. The TILs or PBLs preferably are from the subject. However, they should at least be MHC Class-I restricted to the HLA types the subject possesses. An effective amount of the sensitized cells are then administered to the subject.

PBMCs may be used as the responder cell source of CTL precursors. The appropriate antigen-presenting cells are incubated with peptide, after which the peptide-loaded antigen-presenting cells are then incubated with the responder cell population under optimized culture conditions. Positive CTL activation can be determined by assaying the culture for the presence of CTLs that kill radio-labeled target cells, both specific peptide-pulsed targets as well as target cells expressing endogenously processed forms of the antigen from which the peptide sequence was derived.

The cells can be administered to inhibit the growth of cells of SV-NGEP expressing tumors. In these applications, a therapeutically effective amount of activated antigen presenting cells, or activated lymphocytes, are administered to a subject suffering from a disease, in an amount sufficient to raise an immune response to SV-NGEP-expressing cells. The resulting immune response is sufficient to slow the proliferation of such cells or to inhibit their growth.

In a supplemental method, any of these immunotherapies is augmented by administering a cytokine, such as IL-2, IL-3, IL-6, IL-10, IL-12, IL-15, GM-CSF, interferons.

Diagnostic Methods and Kits

A method is provided herein for the detection of SV-NGEP-expressing prostate cells or prostate tissue in a biological sample. The sample can be any sample that includes SV-NGEP polypeptide or a nucleic acid encoding SV-NGEP polypeptide. Such samples include, but are not limited to, tissue from biopsies, autopsies, and pathology specimens. Biological samples also include sections of tissues, such as frozen sections taken for histological purposes. Biological samples further include body fluids, such as blood, sputum, serum, or urine. A biological sample is typically obtained from a mammal, such as a rat, mouse, cow, dog, guinea pig, rabbit, or primate. In one embodiment the primate is macaque, chimpanzee, or a human. In a further embodiment, the subject has prostate cancer, or is suspected of having prostate cancer. In a specific, non-limiting example, the subject has metastatic prostate cancer. Methods of detection include, for example, radioimmunoassay, sandwich immunoassays (including ELISA), immunofluorescence assays, Western blot, affinity chromatography (affinity ligand bound to a solid phase), and in situ detection with labeled antibodies.

In one embodiment, a method is provided for detecting an SV-NGEP polypeptide. Kits for detecting an SV-NGEP polypeptide of fragment thereof will typically comprise an antibody that specifically binds SV-NGEP. In some embodiments, an antibody fragment, such as an Fv fragment is included in the kit. For in vivo uses, the antibody is preferably an scFv fragment. In a further embodiment, the antibody is labeled (e.g. fluorescent, radioactive, or an enzymatic label).

In one embodiment, a kit includes instructional materials disclosing means of use of an antibody that specifically binds an SV-NGEP polypeptide or fragment thereof (e.g. for detection of SV-NGEP expressing cells in a sample). The instructional materials may be written, in an electronic form (e.g. computer diskette or compact disk) or may be visual (e.g. video files). The kits may also include additional components to facilitate the particular application for which the kit is designed. Thus, for example, the kit may additionally contain means of detecting a label (e.g. enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment of the present invention, the diagnostic kit comprises an immunoassay. Although the details of the immunoassays may vary with the particular format employed, the method of detecting an SV-NGEP polypeptide or fragment thereof in a biological sample generally comprises the steps of contacting the biological sample with an antibody which specifically reacts, under immunologically reactive conditions, to SV-NGEP. The antibody is allowed to specifically bind under immunologically reactive conditions to form an immune complex, and the presence of the immune complex (bound antibody) is detected directly or indirectly.

In an alternative set of embodiments, kits can be provided for detecting nucleic acids encoding NEGP or a fragment thereof in a biological sample. For example, samples from a subject can be tested to determine whether nucleic acids encoding SV-NGEP protein are present. In one embodiment, an amplification procedure is utilized to detect nucleic acids encoding SV-NGEP. In another embodiment, a blotting procedure (e.g. Northern Blot or Dot Blot) is used to detect the presence of nucleic acids encoding SV-NGEP. Thus, a kit can include probes or primers that specifically hybridize to nucleic acids encoding SV-NGEP.

In one embodiment, a kit provides a primer that amplifies nucleic acid encoding SV-NGEP. Conveniently, the amplification is performed by polymerase chain reaction (PCR). A number of other techniques are, however, known in the art and are contemplated for use (for example, see Marshall, U.S. Pat. No. 5,686,272, discloses the amplification of RNA sequences using ligase chain reaction, or "LCR," Landegren et al., *Science* 241:1077, 1988; Wu et al., *Genomics*, 4:569, 1989;

Barany, in *PCR Methods and Applications* 1:5, 1991; and Barany, *Proc. Natl. Acad. Sci. USA* 88:189, 1991). In one specific, non-limiting example, RNA can be reverse transcribed into DNA and then amplified by LCR, PCR, or other methods. An exemplary protocol for conducting reverse transcription of RNA is taught in U.S. Pat. No. 5,705,365. Selection of appropriate primers and PCR protocols are taught, for example, in Innis et al., eds., PCR Protocols 1990 (Academic Press, San Diego, Calif.).

In one embodiment, the kit includes instructional materials disclosing the manner of use for the primer or probe. The kits may also include additional components to facilitate the particular application for which the kit is designed. The kits may additionally include buffers and other reagents routinely used for the practice of a particular method. Such kits and appropriate contents are well known to those of skill in the art.

The disclosure is illustrated by the following non-limiting Examples.

EXAMPLES

Example 1

Identification of Splice Variant of NGEP

Previously, a new gene (NGEP) expressed in prostate cancer and in normal prostate was identified by EST database mining. NGEP is localized at chromosome 2q37.3 on human genome. There are four exons in NGEP (FIG. 1) and the NGEP transcript has conserved polyadenalyzation sequence at the end of the forth exon followed by polyA tail. The Novel Gene Expressed in Prostate (NGEP) sequence shown in International Application No. PCT/US02/36648, filed on Nov. 13, 2002, which claims the benefit of U.S. Provisional Application No. 60/336,308, filed Nov. 14, 2001, both of which are incorporated by reference herein in their entirety.

The NCBI dbEST/CGAP database (see Emmert-Buck et al., *Science* 274:998, 1996; Krizman et al., *Cancer Res.* 56:5380, 1996); Strausberg et al., *Nat. Genet.* 16:415, 1997), was used as a source for cDNA sequences. The ESTs from human tissues and tumors were downloaded from the NCBI EST database. The cDNA libraries that were processed were listed in several websites, including the Unigene Cluster from the NCBI website, amongst others. The EST sequences were clustered and sorted as described before (Vasmatzis et al., *Proc. Natl. Acad. Sci., USA* 95:300, 1998). However, the candidate gene list was updated by using the EST dataset of May, 2000. Two updated candidate lists were prepared, one with the specificity cutoff for prostate of three as before and another with the cutoff value of six.

As disclosed herein, two additional ESTs were identified from prostate cDNA library, which are aligned at the 3' end of NGEP. PCR primers were designed from the sequence of the new ESTs and a radiolabeled probe from the PCR fragment was generated.

Example 2

Expression Analysis of NGEP Splice Variant in Normal Tissues

The expression of the new EST sequence was determined in different normal tissues. Specifically, a multi-tissue Dot blot analysis was performed using a $^{32}$P labeled PCR generated DNA fragment as a probe.

The human multiple tissue RNA blot (RNA Masterblot, Clontech, Palo Alto, Calif.) and Northern blot (Multiple Tissue Northern blot, Human II, Clontech) hybridizations were carried out as described previously (Liu et al., *Biochem. Biophys. Res. Commun.*, 264:833, 1999). Briefly, RNA hybridizations with multiple tissue RNA Dot blot and Northern blot were performed as follows: membranes were pre-hybridized for 2 h in hybridization solution (Hybrisol I; Intergen, Purchase, N.Y.) at 45° C.

The cDNA probe utilized in these studies was produced from a PCR fragment generated using the primer pair:

T483: CAGGACGTCCAGGACGGGAACACCA; (SEQ ID NO:11) and

T484: AGCTTGTTCACTCTGAACCGGC. (SEQ ID NO:12)

The probe was labeled with $^{32}$P by random primer extension (Lofstrand Labs Ltd, Gaithersburg, Md.), added to the membranes and hybridized for 16 hours. The membranes were then washed 2×15 minutes in 2×SSC, 0.1% SDS, at room temperature and then washed 2×15 minutes in 0.5× SSC, 0.1% SDS, at 55° C. Finally the membranes were exposed on x-ray film for 1-2 days. The washing and the autoradiography of the blot were performed as described (Bera et al., *Proc. Natl. Acad. Sci. USA* 99:3058-3063, 2002).

As shown in FIG. 2, among the 76 different samples of normal and fetal tissue examined, the new EST sequence was detected strongly only in prostate sample (E8). The expression was not detectable in any other tissues including essential organs including brain (A1), heart (A4), lung (A8), kidney (A7), and pancreas (B9). The expression profile was similar to the previously reported NGEP expression.

Example 3

Cloning and Analysis of the Spliced Variant of NGEP cDNA

Northern analysis of NGEP detected several bands of different sizes only in the prostate lane. The smallest band was about 900 bp in size. A Northern analysis was performed to determine if the high molecular weight bands, which were detected by the NGEP probe, were also part of the new prostate EST (SV-NGEP). The PCR generated probe that was used for the Dot blot analysis was also used in the experiment described herein. Methods are described in Example 2.

As shown in FIG. 3, two specific bands (approximately 4.4 and 4.6 kb) were detected only in the prostate lane. These two bands were similar in size to the high molecular weight bands observed in NGEP analysis.

Figure 5:
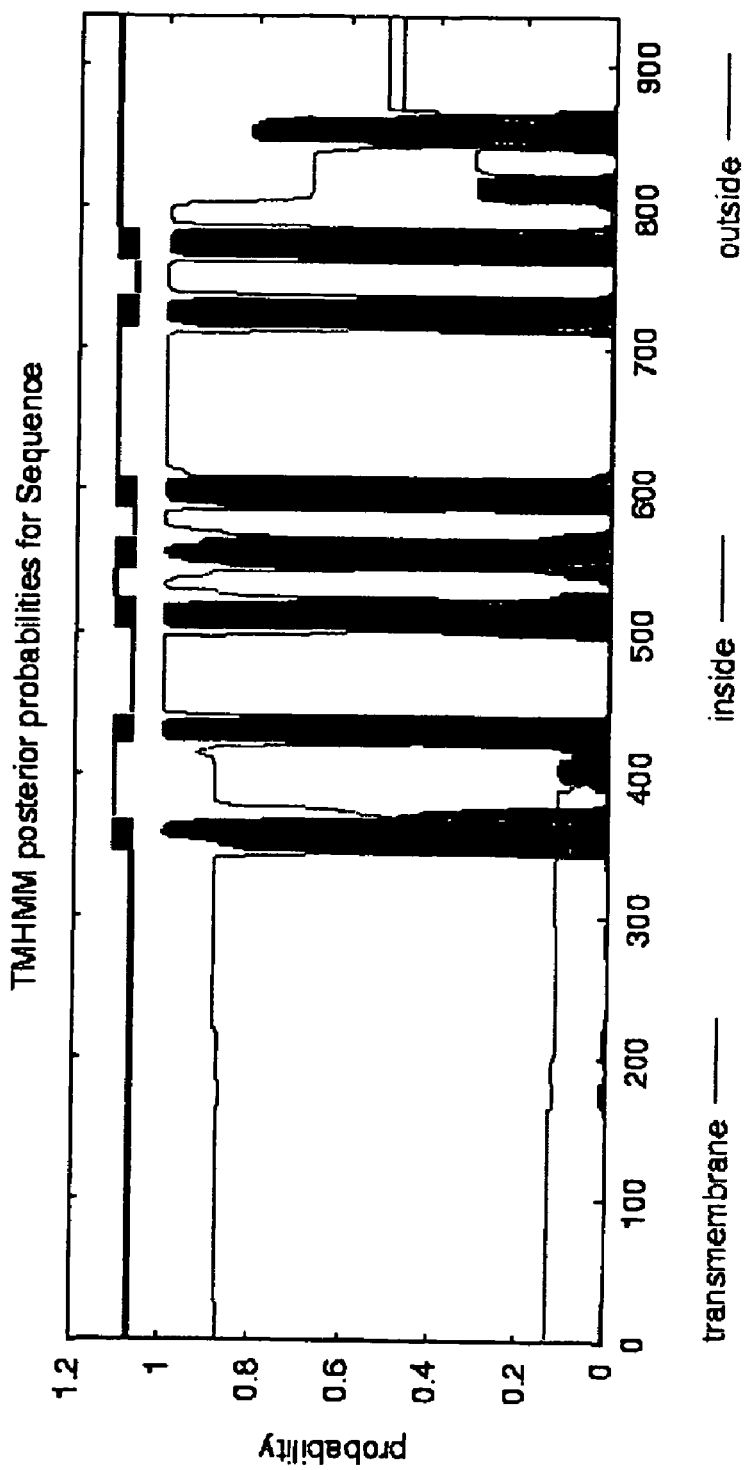
FIG. 5 is a schematic diagram showing the predicted membrane spanning regions of SV-NGEP.

Using PCR primers from NGEP sequence and the sequence from new prostate EST (termed SV-NGEP) about a 2.0 kb cDNA fragment was cloned. Complete nucleotide sequence of the cDNA and the amino acid sequence encoded by this DNA fragment is shown in FIG. 3 and FIG. 4, respectively. The amino acid sequence analysis of the encoded protein using the HMM program which is available on the internet at the Center for Biological Sequence Analysis website (TMHMM server v 2.0) revealed that it had six membrane spanning regions (FIG. 5).

Example 4

Generation of Antibodies to the Extracellular Domain of SV-NGEP

A fusion protein of the extracellular domain of SV-NGEP (amino acids 875 to 933) with rabbit Fc protein was produced in eukaryotic cells. The purified Fc-NGEP fusion protein was used to immunize rabbits and mice. The immunize sera was then tested for its reactivity to SV-NGEP protein by Western blot and fluorescence activated cells sorting (FACS) analysis in cells transfected with plasmid designed to express the SV-NGEP gene. Cells transfected with empty vector was used as negative control for the FACS analysis.

As shown in FIG. 6A-B, a substantial number of cells transfected with SV-NGEP reacted with a representative mouse (FIG. 6A) and rabbit (FIG. 6B) antisera, whereas no reactivity was observed in cells transfected with the empty vector. The antisera from rabbit was tested in a Western blot using protein extract from cells tranfected with SV-NGEP. A specific band of the expected size (100 kDa) was detected. These results indicate that antibodies against the extracellular domain of SV-NGEP can be generated in both mice and rabbits.

Example 5

Expression of NGEP in Prostate Cancer

RNAs from twenty prostate cancers were analyzed. Real time PCR and array analysis was used to detect expression of SV-NGEP in these samples. SV-NGEP was expressed in all specimens tested.

Example 6

Radioimmunoassay to Detect SV-NGEP

The following example sets forth an exemplary protocol for a radioimmunoassay to detect the presence of SV-NGEP in a sample.

Radiolabeling of SV-NGEP

Two and a half micrograms of chemically synthesized or *E. coli* expressed SV-NGEP are labeled with $^{125}$I using the chloramine T method (Hunter and Greenwood, *Nature* 194: 495, 1962). The labeled protein is then purified using a PD-10 column (Amersham Pharmacia Biotech).

Anti-SV-NGEP Antibody

Anti-SV-NGEP antibodies are prepared by using proteinA purified antisera from rabbits immunized with a *Pseudomonas* exotoxin (PE)-SV-NGEP fusion protein using standard techniques (Bruggeman et al., *BioTechniques* 10:202, 1992).

Standard Curve

A standard curve is established by mixing a fixed amount of labeled SV-NGEP (~0.2 ng at about 170 µCi/µg) with different concentrations of unlabeled SV-NGEP (0.1 ng-50 ng) in 250 µl buffer (PBS with 0.25% bovine serum albumin) containing 1 µg of anti-SV-NGEP antibody. The samples are incubated at room temperature for 4 hours. ProteinA sepharose beads are added and incubated for another hour. Finally the beads are collected by centrifugation and washed with buffer 3 times. The remaining bead pellet is measured for radioactivity in a gamma counter.

Sample Measurement

To measure the amount of SV-NGEP in a tissue extract or a protein extract from a cell culture the same procedure is used, but with the sample substituted for the known amounts of the protein used in the standard curve description.

Example 7

Production of an Immune Response Against SV-NGEP in a Primate

The prostate gland of the rhesus monkey is structurally and functionally similar to the human prostate (Wakui et al., *J. Anat.* 181:121, 1992; U.S. Pat. No. 6,165,460). Thus, juvenile male rhesus monkeys (Macaca mulatta), ages 1 to 2 years, are assigned to groups (e.g., three vaccination groups of four animals each, a low dose, a high dose and a control group). One animal from each group is surgically prostatectomized to parallel two situations with regard to potential therapy in humans: (a) prostate intact, with primary and/or metastatic disease; or (b) patients prostatectomized with prostate cancer metastatic deposits. Animals are immunized 3 times over a two month period with a recombinant virus (e.g. a pox virus, see U.S. Pat. No. 6,165,460). For example, a dose of either $1 \times 10^7$ or $1 \times 10^8$ PFU of a recombinant pox virus encoding SV-NGEP is administered to 4 animals by skin scarification. A control vector (e.g. V-Wyeth, $1 \times 10^8$ PFU) is administered to a control group of animals.

Physical examinations are performed on ketamine (Ketamine® HCl, 10 mg/kg I.M.) sedated animals. Rectal temperatures and weights are recorded for each monkey on a weekly basis. The vaccination site is observed and erythema and swelling of the vaccination site are measured by caliper. Each animal is examined for regional lymphadenopathy, hepatomegaly, and splenomegaly. Any other gross abnormalities were also recorded.

Blood is obtained by venipuncture from the femoral vein of ketamine sedated animals before and after each immunization. A complete blood count, differential, hepatic and renal chemistry evaluation is performed on each monkey. Results are compared to normal primate values. Circulating levels of SV-NGEP before and after immunization are analyzed (e.g. by immunoassay or Northern blot).

Prior to each immunization and 2 weeks following each immunization, anti-SV-NGEP antibody is quantified by ELISA. Microtiter plates are coated with purified SV-NGEP (e.g. 100 ng/well,), ovalbumin (100 ng/well, Sigma), or $1 \times 10^7$ PFU/well UV-inactivated V-Wyeth in phosphate buffered saline (PBS). The plates are blocked (e.g. using 2% BSA in PBS), dried, and stored at −20° C. until used. The plates are incubated with serum (e.g. diluted 1:5), as well as a monoclonal antibody for SV-NGEP as a standard control, for 24 hours at 4° C. Plates are washed several times (e.g. with PBS containing 1% BSA), and incubated with a commercially labeled antibody that specifically binds the anti-SV-NGEP monoclonal antibody. An appropriate reagent system is used to visualize antibody binding. For example the antibody is labeled with horseradish peroxidase (HRP), and detected by HRP substrate system (Kirkegaard & Perry Laboratories, Gaithersburg, Md.) according to the manufacture's instructions. The absorbance of each well is read at 405 nm using a Bio-Tek EL310 microplate ELISA reader (Winooski, Vt.).

Sera from each monkey is analyzed by ELISA for immunoreactivity to SV-NGEP. Sera obtained from monkeys prior to vaccination are also analyzed, and are negative for reactivity to SV-NGEP. SV-NGEP specific T cell responses in monkeys immunized with SV-NGEP containing vector or control vector are also analyzed using a lymphoproliferative assays using peripheral blood mononuclear cells.

Example 8

Kit for the Detection of Metastatic Prostate Cancer

Prostate cancer is known to metastasize to other areas of the body, such as bone. Antibodies to an SV-NGEP polypeptide can be used to detect prostate cancer cells at locations other than the prostate.

In order to determine if a metastatic tumor originates in the prostate, the expression of SV-NGEP is assessed. Specifically, a kit is utilized that provides an immunoassay that can be used to confirm that the cancer cells are of prostate origin.

A biological sample of the metastasis is obtained. In one example, the sample is a bone marrow sample. Non-specific immunoreactive sites on biological sample are blocked with a commercially available blocking agent, such as 10% bovine serum albumin in phosphate buffered saline (PBS), for thirty minutes at room temperature. The sample is then contacted with a mouse monoclonal antibody that specifically binds SV-NGEP for an incubation period sufficient to allow formation of an immune complex (e.g. ten minutes to three hours at room temperature in a solution of 1% BSA). The presence of the immune complex (bound antibody) is detected by incubating the sample with a commercially available labeled secondary antibody that specifically binds the SV-NGEP antibody. For example, a fluorescent labeled (e.g. fluorescein isothiocyanate, FITC) goat anti-mouse antibody is diluted 1:100 in PBS/1% BSA and incubated with the sample for an amount of time sufficient to form an immune complex (e.g. ten minutes to about two hours at room temperature). The samples are then processed to determine binding of the second antibody (e.g. detection of fluorescence). A positive signal indicates that the metastasis is of prostate origin.

Example 9

Activation of T Cells Using SV-NGEP

Methods for evaluating immunogenicity of peptides are known. Immunogenicity be evaluated by, for example, evaluation of primary T cell cultures from normal individuals (see, e.g., Wentworth et al., *Mol. Immunol.* 32:603, 1995; Celis, et al., *Proc. Natl. Acad. Sci. USA* 91:2105, 1994; Tsai et al., *J. Immunol.* 158:1796, 1997; Kawashima et al., *Human Immunol.* 59:1, 1998); by immunization of HLA transgenic mice (see, e.g., Wentworth et al., *J. Immunol.* 26:97, 1996; Wentworth et al., *Int. Immunol.* 8:651, 1996; Alexander, et al., *J. Immunol.* 159:4753, 1997), and by demonstration of recall T cell responses from patients who have been effectively vaccinated or who have a tumor (see, e.g., Rehermann et al., *J. Exp. Med.* 181:1047, 1995; Doolan et al., *Immunity* 7:97, 1997; Bertoni et al., J. *Clin. Invest.* 100:503, 1997; Threlkeld et al., *J. Immunol.* 159:1648 1997; Diepolder et al., *J. Virol.* 71:6011, 1997).

In choosing CTL-inducing peptides of interest, peptides with higher binding affinity for Class I HLA molecules can be utilized. Peptide binding is assessed by testing the ability of a candidate peptide to bind to a purified HLA molecule in vitro.

Based on the polypeptide sequence of SV-NGEP, amino acid sequences bearing motifs for any particular HLA molecule can be identified. Peptides including these motifs can be prepared by any of the typical methods (e.g., recombinantly, chemically, etc.). Because SV-NGEP is a self protein, the amino acid sequences bearing HLA binding motifs are those that encode subdominant or cryptic epitopes. Those epitopes are identified by a lower comparative binding affinity for the HLA molecule with respect to other epitopes in the molecule or compared with other molecules that bind to the HLA molecule.

Polypeptides that include an amino acid sequence from SV-NGEP that, in turn, include an HLA binding motif also are useful for eliciting an immune response. This is because, in part, such proteins will be processed by the cell into a peptide that can bind to the HLA molecule and that have an SV-NGEP epitope.

A complex of an HLA molecule and a peptidic antigen acts as the ligand recognized by HLA-restricted T cells (Buus et al., *Cell* 47:1071, 1986; Babbitt et al., *Nature* 317:359, 1985; al., *Cell* 47:1071, 1986; Babbitt et al., *Nature* 317:359, 1985; Townsend and Bodmer, *Annu. Rev. Immunol.* 7:601, 1989; Germain, *Annu. Rev. Immunol.* 11:403, 1993). Through the study of single amino acid substituted antigen analogs and the sequencing of endogenously bound, naturally processed peptides, critical residues that correspond to motifs required for specific binding to HLA antigen molecules have been identified (see, e.g., Southwood et al., *J. Immunol.* 160:3363, 1998; Rammensee et al., *Immunogenetics* 41:178, 1995; Rammensee et al., *J. Curr. Opin. Immunol.* 10:478, 1998; Engelhard, *Curr. Opin. Immunol.* 6:13, 1994; Sette and Grey, *Curr. Opin. Immunol.* 4:79, 1992).

Furthermore, x-ray crystallographic analysis of HLA-peptide complexes has revealed pockets within the peptide binding cleft of HLA molecules which accommodate, in an allele-specific mode, residues borne by peptide ligands; these residues in turn determine the HLA binding capacity of the peptides in which they are present (e.g., Madden, *Annu. Rev. Immunol.* 13:587, 1995; Smith, et al., *Immunity* 4:203, 1996; Fremont et al., *Immunity* 8:305, 1998; Stern et al., *Structure* 2:245, 1994; Jones, *Curr. Opin. Immunol.* 9:75, 1997; Brown et al., *Nature* 364:33, 1993).

Accordingly, the definition of Class I and Class II allele-specific HLA binding motifs, or Class I or Class II supermotifs allows identification of regions within SV-NGEP that have the potential of binding particular HLA molecules.

One method of identifying genes encoding antigenic determinants is as follows: Tumor infiltrating lymphocytes (TILs) from a subject with prostate cancer are grown and tested for the ability to recognize the autologous cancer in vitro. These TILs are administered to the subject to identify the ones that result in tumor regression. The TILs are used to screen expression libraries for genes that express epitopes recognized by the TILs. Subjects then are immunized with these genes. Alternatively, lymphocytes are sensitized in vitro against antigens encoded by these genes. Then the sensitized lymphocytes are adoptively transferred into subjects and tested for their ability to cause tumor regression. Rosenberg et al., *Immunol. Today* 18:175, 1997.

To ensure that SV-NGEP elicits a CTL response to SV-NGEP in vivo (or, in the case of Class II epitopes, elicits helper T cells that cross-react with the wild type peptides), the SV-NGEP can be used to immunize T cells in vitro from individuals of the appropriate HLA allele. Thereafter, the immunized cells' capacity to induce lysis of SV-NGEP-sensitized target cells is evaluated.

More generally, SV-NGEP peptides can be synthesized and tested for their ability to bind to HLA proteins and to activate HTL or CTL responses, or both.

Conventional assays utilized to detect T cell responses include proliferation assays, lymphokine secretion assays, direct cytotoxicity assays, and limiting dilution assays. For example, antigen-presenting cells that have been incubated with a peptide can be assayed for the ability to induce CTL responses in responder cell populations.

PBMCs can be used as the responder cell source of CTL precursors. The appropriate antigen-presenting cells are incubated with peptide, after which the peptide-loaded antigen-presenting cells are then incubated with the responder cell population under optimized culture conditions. Positive CTL activation can be determined by assaying the culture for the presence of CTLs that kill radiolabeled target cells, both specific peptide-pulsed targets as well as target cells expressing endogenously processed forms of the antigen from which the peptide sequence was derived.

A method which allows direct quantification of antigen-specific T cells is staining with Fluorescein-labeled HLA tetrameric complexes (Altman et al., *Proc. Natl. Acad. Sci USA* 90:10330, 1993; Altman et al., *Science* 274:94, 1996). Alternatively, staining for intracellular lymphokines, interferon-γ release assays or ELISPOT assays, can be used to evaluate T cell responses.

CTL activation may be assessed using such techniques known to those in the art such as T cell proliferation and secretion of lymphokines, e.g. IL-2 (see e.g. Alexander et al., *Immunity* 1:751-761, 1994).

In one specific, non-limiting example, transgenic mice that express a chimeric human Class 1 major histocompatibility (MHC) Class 1 molecule composed of the α1 and α2 domains of HLA-A2.1 and the α3, transmembrane and cytoplamic domains of H2-kb HLA transgenic mice (see, e.g., Wentworth et al., *J. Immunol.* 26:97, 1996; Wentworth et al., *Int. Immunol.* 8:651, 1996; Alexander et al., *J. Immunol.* 159: 4753, 1997) are immunized with plasmid DNA encoding SV-NGEP. Specifically, each mouse is injected intramuscularly with 100 μg of plasmid five times every three weeks. After the final immunization CD8+ cells are partially purified using antibody-coated magnetic beads and re-stimulated with syngeneic spleenocytes for one week in T-stim media. Specifically, cells from the immunized transgenic mice are co-cultured either with stimulating spleenocytes (e.g., $3.5 \times 10^6$ spleenocytes) pulsed with various concentrations (100, 0.1 or 0.0001 μM) SV-NGEP peptide or in the presence of free peptide (1 μM) in a 24 well plate containing 2 ml of a 1:1 mixture of RPMI1640 media and Eagle-Hanks amino acid medium supplemented with L-glutamine, sodium pyruvate, non-essential amino acids, antibiotics penicillin, streptomycin, $5 \times 10^{-5}$ M 2-mercaptoetanol, 10% fetal calf serum, and 10% T-stim (Collaborative Biomedical Products, Bedford, Mass.). On day seven, a cytoxoic T lymphocyte (CTL) assay is carried out using LnCAP cells expressing SV-NGEP as target cells in the presence of peptides fragments of SV-NGEP. For example, LnCAP target cells ($1 \times 10^6$) are labeled with 300 μCi of $Na_2^{51}CrO_4$ in 200-250 μl for 2 hours at 37° C. For test samples, targets are pulsed with peptide during labeling. Cells are then washed and added to wells along with the appropriate number of effector cells in 96-well round bottom plates. After four hours, supernatents are harvested and counted in an ISOMEDIC gamma counter (ICN). The mean of triplicate samples and percent of $^{51}Cr$ release is calculated (see Alexander-Miller et al., *Proc. Natl. Acad. Sci. USA* 93:4102). The results demonstrate that SV-NGEP peptides can be used to induce cytotoxic activity against LnCAP cells.

It will be apparent that the precise details of the methods or compositions described may be varied or modified without departing from the spirit of the described invention. We claim all such modifications and variations that fall within the scope and spirit of the claims below.

The invention claimed is:

1. An isolated polypeptide comprising:
   (1) at least eight consecutive amino acids of amino acids 157-933 of SEQ ID NO: 1, wherein the isolated polypeptide is eight to ten amino acids in length and binds a Major Histocompatability Complex (MHC) molecule; or
   (2) the amino acid sequence set forth as SEQ ID NO: 1.

2. The isolated polypeptide of claim 1, comprising an amino acid sequence as set forth as SEQ ID NO: 1.

3. The isolated polypeptide of claim 1, comprising the at least eight consecutive amino acids of amino acids 157-933 of SEQ ID NO: 1, wherein the isolated polypeptide is eight to ten amino acids in length and binds an MHC molecule.

4. An isolated polynucleotide encoding the polypeptide of claim 3.

5. The isolated polynucleotide of claim 4 operably linked to a promoter.

6. An expression vector comprising the polynucleotide of claim 5.

7. An isolated host cell transfected with the polynucleotide of claim 5.

8. The isolated host cell of claim 7, wherein the host cell is a mammalian cell.

9. A composition comprising the polypeptide of claim 1 in a carrier.

10. A fusion protein, comprising a) the polypeptide of claim 1, wherein the polypeptide comprises at least eight consecutive amino acids of amino acids 157-933 of SEQ ID NO:1, wherein the polypeptide is eight to ten amino acids in length and binds a Major Histocompatability Complex (MHC) molecule; and b) a heterologous polypeptide.

11. An isolated polypeptide consisting of the amino acid sequence set forth as amino acids 157-933 of SEQ ID NO: 1.

12. An isolated polypeptide consisting of the amino acid sequence set forth as one of SEQ ID NO: 3-10.

13. An isolated polynucleotide comprising the nucleic acid sequence as set forth as SEQ ID NO: 2, or a degenerate variant thereof.

14. The isolated polynucleotide of claim 13, operably linked to a promoter.

15. An expression vector comprising the polynucleotide of claim 13.

16. An isolated host cell transfected with the polynucleotide of claim 13.

17. The isolated host cell of claim 16, wherein the host cell is a mammalian cell.

18. A method for detecting prostate cells in a subject comprising detecting expression of the polynucleotide of claim 13 in a sample from the subject, wherein detection of the expression of the polynucleotide indicates the presence of the prostate cells.

19. The method of claim 18, wherein detecting the expression of the polynucleotide comprises detecting mRNA in a Northern Blot analysis, an RNA Dot blot, or a reverse transcriptase polymerase chain reaction (RT-PCR) assay.

20. A method for producing an immune response to the polypeptide of claim 1, the method comprising
   administering to a subject an effective amount of the polypeptide of claim 1,
   thereby producing the immune response to the polypeptide.

21. The method of claim 20, wherein the immune response comprises production of antibodies.

* * * * *

SEQUENCE LISTING

<160> NUMBER OF SEQ ID NOS: 12

<210> SEQ ID NO 1
<211> LENGTH: 933
<212> TYPE: PRT
<213> ORGANISM: Artificial Sequence
<220> FEATURE:
<223> OTHER INFORMATION: Splice Variant-Novel Gene Expressed in Prostate

<400> SEQUENCE: 1

Met Arg Met Ala Ala Thr Ala Trp Ala Gly Leu Gln Gly Pro Pro Leu
1               5                   10                  15

Pro Thr Leu Cys Pro Ala Val Arg Thr Gly Leu Tyr Cys Arg Asp Gln
            20                  25                  30

Ala His Ala Glu Arg Trp Ala Met Thr Ser Glu Thr Ser Ser Gly Ser
        35                  40                  45

His Cys Ala Arg Ser Arg Met Leu Arg Arg Arg Ala Gln Glu Glu Asp
    50                  55                  60

Ser Thr Val Leu Ile Asp Val Ser Pro Pro Glu Ala Glu Lys Arg Gly
65                  70                  75                  80

Ser Tyr Gly Ser Thr Ala His Ala Ser Glu Pro Gly Gly Gln Gln Ala
                85                  90                  95

Ala Ala Cys Arg Ala Gly Ser Pro Ala Lys Pro Arg Ile Ala Asp Phe
            100                 105                 110

Val Leu Val Trp Glu Glu Asp Leu Lys Leu Asp Arg Gln Gln Asp Ser
        115                 120                 125

-continued

```
Ala Ala Arg Asp Arg Thr Asp Met His Arg Thr Trp Arg Glu Thr Phe
    130                 135                 140
Leu Asp Asn Leu Arg Ala Ala Gly Leu Cys Val Asp Gln Gln Asp Val
145                 150                 155                 160
Gln Asp Gly Asn Thr Thr Val His Tyr Ala Leu Leu Ser Ala Ser Trp
                165                 170                 175
Ala Val Leu Cys Tyr Tyr Ala Glu Asp Leu Arg Leu Lys Leu Pro Leu
            180                 185                 190
Gln Glu Leu Pro Asn Gln Ala Ser Asn Trp Ser Ala Gly Leu Leu Ala
        195                 200                 205
Trp Leu Gly Ile Pro Asn Val Leu Leu Glu Val Val Pro Asp Val Pro
    210                 215                 220
Pro Glu Tyr Tyr Ser Cys Arg Phe Arg Val Asn Lys Leu Pro Arg Phe
225                 230                 235                 240
Leu Gly Ser Asp Asn Gln Asp Thr Phe Phe Thr Ser Thr Lys Arg His
                245                 250                 255
Gln Ile Leu Phe Glu Ile Leu Ala Lys Thr Pro Tyr Gly His Glu Lys
            260                 265                 270
Lys Asn Leu Leu Gly Ile His Gln Leu Leu Ala Glu Gly Val Leu Ser
        275                 280                 285
Ala Ala Phe Pro Leu His Asp Gly Pro Phe Lys Thr Pro Pro Glu Gly
    290                 295                 300
Pro Gln Ala Pro Arg Leu Asn Gln Arg Gln Val Leu Phe Gln His Trp
305                 310                 315                 320
Ala Arg Trp Gly Lys Trp Asn Lys Tyr Gln Pro Leu Asp His Val Arg
                325                 330                 335
Arg Tyr Phe Gly Glu Lys Val Ala Leu Tyr Phe Ala Trp Leu Gly Phe
            340                 345                 350
Tyr Thr Gly Trp Leu Leu Pro Ala Ala Val Val Gly Thr Leu Val Phe
        355                 360                 365
Leu Val Gly Cys Phe Leu Val Phe Ser Asp Ile Pro Thr Gln Glu Leu
    370                 375                 380
Cys Gly Ser Lys Asp Ser Phe Glu Met Cys Pro Leu Cys Leu Asp Cys
385                 390                 395                 400
Pro Phe Trp Leu Leu Ser Ser Ala Cys Ala Leu Ala Gln Ala Gly Arg
                405                 410                 415
Leu Phe Asp His Gly Gly Thr Val Phe Phe Ser Leu Phe Met Ala Leu
            420                 425                 430
Trp Ala Val Leu Leu Leu Glu Tyr Trp Lys Arg Lys Ser Ala Thr Leu
        435                 440                 445
Ala Tyr Arg Trp Asp Cys Ser Asp Tyr Glu Asp Thr Glu Glu Arg Pro
    450                 455                 460
Arg Pro Gln Phe Ala Ala Ser Ala Pro Met Thr Ala Pro Asn Pro Ile
465                 470                 475                 480
Thr Gly Glu Asp Glu Pro Tyr Phe Pro Glu Arg Ser Arg Ala Arg Arg
                485                 490                 495
Met Leu Ala Gly Ser Val Val Ile Val Val Met Val Ala Val Val Val
            500                 505                 510
Met Cys Leu Val Ser Ile Ile Leu Tyr Arg Ala Ile Met Ala Ile Val
        515                 520                 525
Val Ser Arg Ser Gly Asn Thr Leu Leu Ala Ala Trp Ala Ser Arg Ile
    530                 535                 540
Ala Ser Leu Thr Gly Ser Val Val Asn Leu Val Phe Ile Leu Ile Leu
```

-continued

```
                545                 550                 555                 560

Ser Lys Ile Tyr Val Ser Leu Ala His Val Leu Thr Arg Trp Glu Met
                565                 570                 575

His Arg Thr Gln Thr Lys Phe Glu Asp Ala Phe Thr Leu Lys Val Phe
                580                 585                 590

Ile Phe Gln Phe Val Asn Phe Tyr Ser Pro Val Tyr Ile Ala Phe
                595                 600                 605

Phe Lys Gly Arg Phe Val Gly Tyr Pro Gly Asn Tyr His Thr Leu Phe
                610                 615                 620

Gly Val Arg Asn Glu Glu Cys Ala Ala Gly Gly Cys Leu Ile Glu Leu
625                 630                 635                 640

Ala Gln Glu Leu Leu Val Ile Met Val Gly Lys Gln Val Ile Asn Asn
                645                 650                 655

Met Gln Glu Val Leu Ile Pro Lys Leu Lys Gly Trp Trp Gln Lys Phe
                660                 665                 670

Arg Leu Arg Ser Lys Lys Arg Lys Ala Gly Ala Ser Ala Gly Ala Ser
                675                 680                 685

Gln Gly Pro Trp Glu Asp Asp Tyr Glu Leu Val Pro Cys Glu Gly Leu
                690                 695                 700

Phe Asp Glu Tyr Leu Glu Met Val Leu Gln Phe Gly Phe Val Thr Ile
705                 710                 715                 720

Phe Val Ala Ala Cys Pro Leu Ala Pro Leu Phe Ala Leu Leu Asn Asn
                725                 730                 735

Trp Val Glu Ile Arg Leu Asp Ala Arg Lys Phe Val Cys Glu Tyr Arg
                740                 745                 750

Arg Pro Val Ala Glu Arg Ala Gln Asp Ile Gly Ile Trp Phe His Ile
                755                 760                 765

Leu Ala Gly Leu Thr His Leu Ala Val Ile Ser Asn Ala Phe Leu Leu
                770                 775                 780

Ala Phe Ser Ser Asp Phe Leu Pro Arg Ala Tyr Tyr Arg Trp Thr Arg
785                 790                 795                 800

Ala His Asp Leu Arg Gly Phe Leu Asn Phe Thr Leu Ala Arg Ala Pro
                805                 810                 815

Ser Ser Phe Ala Ala Ala His Asn Arg Thr Cys Arg Tyr Arg Ala Phe
                820                 825                 830

Arg Asp Asp Asp Gly His Tyr Ser Gln Thr Tyr Trp Asn Leu Leu Ala
                835                 840                 845

Ile Arg Leu Ala Phe Val Ile Val Phe Glu His Val Val Phe Ser Val
                850                 855                 860

Gly Arg Leu Leu Asp Leu Leu Val Pro Asp Ile Pro Glu Ser Val Glu
865                 870                 875                 880

Ile Lys Val Lys Arg Glu Tyr Tyr Leu Ala Lys Gln Ala Leu Ala Glu
                885                 890                 895

Asn Glu Val Leu Phe Gly Thr Asn Gly Thr Lys Asp Glu Gln Pro Lys
                900                 905                 910

Gly Ser Glu Leu Ser Ser His Trp Thr Pro Phe Thr Val Pro Lys Ala
                915                 920                 925

Ser Gln Leu Gln Gln
      930

<210> SEQ ID NO 2
<211> LENGTH: 3308
<212> TYPE: DNA
<213> ORGANISM: Artificial Sequence
```

```
<220> FEATURE:
<223> OTHER INFORMATION: Splice Variant-Novel Gene Expressed in Prostate

<400> SEQUENCE: 2
aaaagataga tcctgctcca ggagccggga agcctcgccc tggccagctg tgctgggcac      60
ctcccctgcc tgcttcctgg cccacttgca ggcaaggtga gggcatgcga atggctgcca     120
ctgcctgggc ggggctccaa gggccacccc tccccaccct ctgtcccgca gtgaggacgg     180
gactctactg ccgagaccag gctcacgctg agaggtgggc catgacctcc gagacctctt     240
ccggaagcca ctgtgccagg agcaggatgc tgcggcgacg ggcccaggaa gaggacagca     300
ccgtcctgat cgatgtgagc cccctgagg cagagaagag gggctcttac gggagcacag      360
cccacgcctc ggagccaggt ggacagcaag cggccgcctg cagagctggg agtcctgcca     420
agccccggat cgcagacttc gtcctcgttt gggaggagga cctgaagcta gacaggcagc     480
aggacagtgc cgcccgggac agaacagaca tgcacaggac ctggcgggag acttttctgg     540
ataatcttcg tgcggctggg ctgtgtgtag accagcagga cgtccaggac gggaacacca     600
cagtgcacta cgccctcctc agcgcctcct gggctgtgct ctgctactac gccgaagacc     660
tgcgcctgaa gctgcccttg caggagttac ccaaccaggc ctccaactgg tcggccggcc     720
tgctggcatg gctgggcatc cccaacgtcc tgctggaggt tgtgccagac gtaccccccg     780
agtactactc ctgccggttc agagtgaaca agctgccacg cttcctcggg agtgacaacc     840
aggacacctt cttcacaagc accaagaggc accaaattct gtttgagatc ctggccaaga     900
ccccgtatgg ccacgagaag aaaaacctgc ttgggatcca ccagctgctg gcagagggtg     960
tcctcagtgc cgccttcccc ctgcatgacg gccccttcaa gacgccccca gagggcccgc    1020
aggctccacg cctcaaccag cgccaagtcc ttttccagca ctgggcgcgc tggggcaagt    1080
ggaacaagta ccagcccctg gaccacgtgc gcaggtactt cggggagaag gtggccctct    1140
acttcgcctg gctcgggttt tacacaggct ggctcctgcc agcggcagtg gtgggcacac    1200
tggtgttcct ggtgggctgc ttcctggtgt tctcagacat acccacgcag gaactgtgtg    1260
gcagcaagga cagcttcgag atgtgcccac tttgcctcga ctgccctttc tggctgctct    1320
ccagcgcctg tgccctggcc caggccggcc ggctgttcga ccacggcggc accgtgttct    1380
tcagcttgtt catggcactg tgggccgtgc tgctgctgga gtactggaag cggaagagcg    1440
ccacgctggc ctaccgctgg gactgctctg actacgagga cactgaggag aggcctcggc    1500
cccagtttgc cgcctcagcc cccatgacag ccccgaaccc catcacgggt gaggacgagc    1560
cctacttccc tgagaggagc cgcgcgcgcc gcatgctggc cggctctgtg gtgatcgtgg    1620
tgatggtggc cgtggtggtc atgtgcctcg tgtctatcat cctgtaccgt gccatcatgg    1680
ccatcgtggt gtccaggtcg ggcaacaccc ttctcgcagc ctgggcctct cgcatcgcca    1740
gcctcacggg gtctgtagtg aacctcgtct tcatcctcat cctctccaag atctatgtat    1800
ccctggccca cgtcctgaca cgatgggaaa tgcaccgcac ccagaccaag ttcgaggacg    1860
ccttcacccct caaggtgttc atcttccagt tcgtcaactt ctactcctca cccgtctaca    1920
ttgccttctt caagggcagg tttgtgggat acccaggcaa ctaccacacc ttgtttggag    1980
tccgcaatga ggagtcgcgc gctggaggct cctgatcga gctggcacag gagctcctgg    2040
tcatcatggt gggcaagcag gtcatcaaca acatgcagga ggtcctcatc ccgaagctaa    2100
agggctggtg gcagaagttc cggcttcgct ccaagaagag gaaggcggga gcttctgcag    2160
gggctagcca ggggccctgg gaggacgact atgagcttgt gccctgtgag ggtctgtttg    2220
```

-continued

```
acgagtacct ggaaatggtg ctgcagttcg gcttcgtcac catcttcgtg gccgcctgtc    2280
cgctcgcgcc gctcttcgcc ctgctcaaca actgggtgga gatccgcttg gacgcgcgca    2340
agttcgtctg cgagtaccgg cgccctgtgg ccgagcgcgc ccaggacatc ggcatctggt    2400
tccacatcct ggcgggcctc acgcacctgg cggtcatcag caacgccttc ctcctggcct    2460
tctcgtccga cttcctgccg cgcgcctact accggtggac ccgcgcccac gacctgcgcg    2520
gcttcctcaa cttcacgctg gcgcgagccc cgtcctcctt cgccgccgcg cacaaccgca    2580
cgtgcaggta tcgggctttc cgggatgacg atggacatta ttcccagacc tactggaatc    2640
ttcttgccat ccgcctggcc ttcgtcattg tgtttgagca tgtggttttc tccgttggcc    2700
gcctcctgga cctcctggtg cctgacatcc cagagtctgt ggagatcaaa gtgaagcggg    2760
agtactacct ggctaagcag gcactggctg agaatgaggt tcttttttgga acgaacggaa    2820 caaaggatga gcagcccaag ggctcagagc tcagctccca ctggacaccc ttcacggttc    2880
ccaaggccag ccagctgcag cagtgacgcc tggaaggaca tctggtggtc cttaggggag    2940
tggcccctcc tgagccctgc gagcagcgtc cttttcctct tccctcaggc agcggctgtg    3000
tgaaccgctg gctgctgttg tgcctcatct ctgggcacat tgcctgcttc ccccagcgc    3060 cggcttctct cctcagagcg cctgtcactc catccccggc agggagggac cgtcagctca    3120
caaggccctc tttgtttcct gctcccagac ataagcccaa ggggcccctg cacccaaggg    3180
accctgtccc tcggtggcct ccccaggccc ctggacacga cagttctcct caggcaggtg    3240
ggctttgtgg tcctcgccgc ccctggccac atcgccctct cctcttacac ctggtgacct    3300
tcgaatgt                                                            3308
```

<210> SEQ ID NO 3
<211> LENGTH: 9
<212> TYPE: PRT
<213> ORGANISM: Artificial Sequence
<220> FEATURE:
<223> OTHER INFORMATION: Splice Variant-Novel Gene Expressed in Prostate

<400> SEQUENCE: 3

Ser Leu Phe Met Ala Leu Trp Ala Val
1               5

<210> SEQ ID NO 4
<211> LENGTH: 9
<212> TYPE: PRT
<213> ORGANISM: Artificial Sequence
<220> FEATURE:
<223> OTHER INFORMATION: Splice Variant-Novel Gene Expressed in Prostate

<400> SEQUENCE: 4

Val Leu Leu Glu Val Val Pro Asp Val
1               5

<210> SEQ ID NO 5
<211> LENGTH: 9
<212> TYPE: PRT
<213> ORGANISM: Artificial Sequence
<220> FEATURE:
<223> OTHER INFORMATION: Splice Variant-Novel Gene Expressed in Prostate

<400> SEQUENCE: 5

Ala Leu Leu Ser Ala Ser Trp Ala Val
1               5

<210> SEQ ID NO 6

```
<211> LENGTH: 9
<212> TYPE: PRT
<213> ORGANISM: Artificial Sequence
<220> FEATURE:
<223> OTHER INFORMATION: Splice Variant-Novel Gene Expressed in Prostate

<400> SEQUENCE: 6

Leu Leu Ala Ile Arg Leu Ala Phe Val
1               5

<210> SEQ ID NO 7
<211> LENGTH: 9
<212> TYPE: PRT
<213> ORGANISM: Artificial Sequence
<220> FEATURE:
<223> OTHER INFORMATION: Splice Variant-Novel Gene Expressed in Prostate

<400> SEQUENCE: 7

Ile Leu Ile Leu Ser Lys Ile Tyr Val
1               5

<210> SEQ ID NO 8
<211> LENGTH: 9
<212> TYPE: PRT
<213> ORGANISM: Artificial Sequence
<220> FEATURE:
<223> OTHER INFORMATION: Splice Variant-Novel Gene Expressed in Prostate

<400> SEQUENCE: 8

Ile Leu Phe Glu Ile Leu Ala Lys Thr
1               5

<210> SEQ ID NO 9
<211> LENGTH: 9
<212> TYPE: PRT
<213> ORGANISM: Artificial Sequence
<220> FEATURE:
<223> OTHER INFORMATION: Splice Variant-Novel Gene Expressed in Prostate

<400> SEQUENCE: 9

Trp Leu Leu Ser Ser Ala Cys Ala Leu
1               5

<210> SEQ ID NO 10
<211> LENGTH: 9
<212> TYPE: PRT
<213> ORGANISM: Artificial Sequence
<220> FEATURE:
<223> OTHER INFORMATION: Splice Variant-Novel Gene Expressed in Prostate

<400> SEQUENCE: 10

Lys Ile Tyr Val Ser Leu Ala His Val
1               5

<210> SEQ ID NO 11
<211> LENGTH: 25
<212> TYPE: DNA
<213> ORGANISM: Artificial Sequence
<220> FEATURE:
<223> OTHER INFORMATION: Oligonucleotide primer/probe

<400> SEQUENCE: 11
caggacgtcc aggacgggaa cacca                                              25

<210> SEQ ID NO 12
<211> LENGTH: 22
<212> TYPE: DNA
```

```
-continued

<213> ORGANISM: Artificial Sequence
<220> FEATURE:
<223> OTHER INFORMATION: Oligonucleotide primer/probe

<400> SEQUENCE: 12
agcttgttca ctctgaaccg gc                                              22
```